(12) United States Patent  
Ribi

(10) Patent No.: US 7,514,262 B2  
(45) Date of Patent: Apr. 7, 2009

(54) PLURAL INTRINSIC EXPIRATION INITIATION APPLICATION INDICATORS

(75) Inventor: Hans O. Ribi, Hillsborough, CA (US)

(73) Assignee: CMC Daymark Corporation, Bowling Green, OH (US)

( * ) Notice: Subject to any disclaimer, the term of this patent is extended or adjusted under 35 U.S.C. 154(b) by 717 days.

(21) Appl. No.: 10/932,628

(22) Filed: Sep. 2, 2004

(65) Prior Publication Data

US 2005/0037498 A1     Feb. 17, 2005

Related U.S. Application Data

(63) Continuation-in-part of application No. 10/226,379, filed on Aug. 23, 2002, now Pat. No. 6,787,108.

(60) Provisional application No. 60/369,309, filed on Apr. 2, 2002.

(51) Int. Cl.  
*G01N 31/00*     (2006.01)

(52) U.S. Cl. .................. 436/2; 436/1; 422/56; 422/57; 422/58; 116/206; 116/207; 374/102

(58) Field of Classification Search .................. 422/56, 422/57, 82.12; 436/1, 2, 7; 374/102; 116/206, 116/207  
See application file for complete search history.

(56) References Cited

U.S. PATENT DOCUMENTS

| | | | |
|---|---|---|---|
| 3,954,011 A | 5/1976 | Manske | |
| 3,999,946 A | 12/1976 | Patel et al. | |
| 4,195,057 A * | 3/1980 | Patel | 422/56 |
| 4,195,058 A * | 3/1980 | Patel | 422/56 |
| 4,228,126 A | 10/1980 | Patel et al. | |
| 4,238,352 A | 12/1980 | Patel | |
| 4,276,190 A * | 6/1981 | Patel | 252/408.1 |
| 4,298,348 A * | 11/1981 | Ivory | 436/7 |
| 4,339,951 A | 7/1982 | Yee et al. | |
| 4,735,745 A | 4/1988 | Preziosi et al. | |
| 5,045,283 A * | 9/1991 | Patel | 422/56 |
| 5,057,434 A | 10/1991 | Prusik et al. | |
| 5,085,801 A | 2/1992 | Thierry et al. | |
| 5,364,132 A | 11/1994 | Haas et al. | |
| 5,642,605 A | 7/1997 | Tenner et al. | |
| 5,667,303 A | 9/1997 | Arens et al. | |
| 5,685,641 A | 11/1997 | Ribi | |
| 5,790,718 A | 8/1998 | Tenner et al. | |
| 5,805,245 A | 9/1998 | Davis | |
| 5,918,981 A | 7/1999 | Ribi | |
| 2002/0034475 A1 | 3/2002 | Ribi | |

* cited by examiner

*Primary Examiner*—Lyle A Alexander  
*Assistant Examiner*—Dennis M White  
(74) *Attorney, Agent, or Firm*—Emch, Schaffer, Schaub & Porcello Co., L.P.A.

(57) ABSTRACT

A device and method for monitoring the expiration of goods includes a substrate, a coating of polydiacetylene, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour and an activating agent on a portion but not all of said coating.

16 Claims, 6 Drawing Sheets

PLURAL INTRINSIC EXPIRATION INITIATION APPLICATION INDICATORS

CROSS-REFERENCE TO RELATED APPLICATION

This application is a continuation-in-part of application Ser. No. 10/226,379 filed Aug. 23, 2002, now U.S. Pat. No. 6,787,108 and is based upon and claims the benefit of Provisional Patent Application Ser. No. 60/369,309 filed Apr. 2, 2002.

BACKGROUND OF THE INVENTION

There is a general need to know whether perishable products and materials have or have not expired prior to consumption or use. For example, it is important to know in restaurants that uncooked meats and poultry have been properly stored at low temperatures and have not exceeded the time frame necessary to maintain freshness. Proportioned foods are periodically turned over and it is critical to monitor the timing and turnover rate accurately to ensure patron safety. In food service organizations, large quantities of perishable foods must be inventoried in preparation for designated preparations. Often large pans, containers, and vats must be periodically used and cycled. It is therefore essential to monitor directly the time and temperature history of perishable food items to ensure maximum freshness and minimum potential pathogenic colonization.

There is concern by food and beverage producers that the products they produce are properly handled throughout the distribution cycle and that safe time and storage temperatures are maintained. It is desirable that at the specific time a perishable item is produced that the time and temperature profile of the food item be monitored cost effectively and directly without the need of employing complicated monitoring equipment or devices which require special handling and storage.

Although dating and color labeling can be used as a means to distinguish and inventory a particular perishable item, complications arise in keeping track of dates, knowing the correct date used, correlating a future date with the present date and remembering the meaning of a particular color which is intended to indicate a particular date of use. It is generally complicated and often inaccurate when relying on an indirect inventorying method to determine when a particular perishable item should or should not be used.

Inventorying methods do not integrate the time and temperature history of a particular item.

Desirably a device capable of accurately indicating the time and temperature history of a perishable product would find practical use if the device could be initiated for monitoring precisely at the time when the perishable product is to be stored in preparation for serving in a coming period. The initiation process should be able to be initiated at the time intended and not well in advance of use. Advance preparation and initiation of such a device may defeat the utility since a means to store such a device may lead to questions about the very questions that the device is intended to monitor.

It is of particular interest to provide a continuum of answers as to the storage and treatment of perishable products. Perishable items typically undergo exposure to various temperature and other storage conditions as well as changes in temperature during preparation, cooking, cooling, and subsequent storage. It is often desirable to monitor and determine the condition of a particular perishable item for food safety, palatability, thoroughness of cooking, and integrity during subsequent storage. Indicators capable of following and reporting the conditions of perishables during the continuum of conditions provide a variety of advantages over devices, thermometers, discrete monitoring or the like which are only capable of reporting one parameter of a condition which a perishable item is exposed to.

Ideally, a simple indicating device capable of a plurality of monitoring capabilities should be simple to use, accurate to interpret and provide only a minimal incremental expense to the overall cost of the perishable item to be monitored.

SUMMARY OF THE INVENTION

Plural intrinsic expiration initiation application indicators are provided comprising an initiation means in which a soluble unreacted composition is applied to a substrate surface and is capable of monitoring/indicating multiple sequential or simultaneous processes. Initiation of the indication process is achieved by evaporation of a solvent and formation of a solid phase of the unreacted composition. When the composition forms a solid, it is intrinsically reactive to its thermal environment resulting in polymerization and subsequent color formation that can measure environmental parameters. The degree of color formation and the intrinsic color hue is a function of the temperature environment to which the substrate and indicating means are subjected. The degree of color formation and color hue can be calibrated to both a schedule for expiration and to have the plural ability to indicate environmental exposed temperatures. Subsequent environmental conditions can be monitored wherein the device can further change color in response to a plurality of differential environmental conditions an item is exposed to. Various substrates, formats and devices for delivering the soluble unreacted composition may be employed for a variety of situations requiring monitoring of expiration of an item of interest.

PLURAL INTRINSIC EXPIRATION INDICATION CHEMISTRIES

Figure 1A:
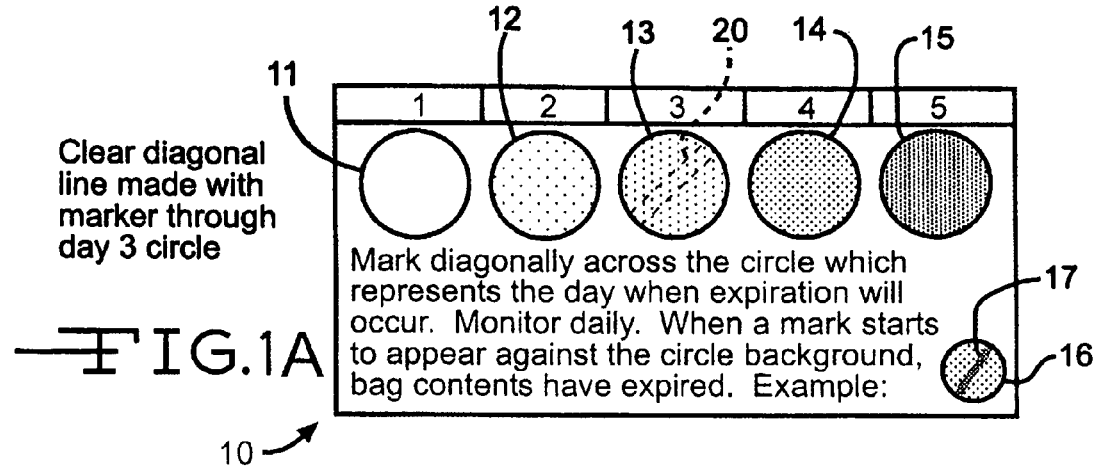
FIG. 1A shows a label of the present invention designating a food of the type having an expiration of three days from date of receipt when stored in a refrigerator.

Plural intrinsic expiration indication chemistries involve the process of transforming a formulation from an inactive form to an activated form at a specific time desired. Materials which can be transformed from an inactive soluble form to an active insoluble form are desirable since their state from solution state to a solid state can serve as an activating process. Further, it is desirable to utilize a composition which is able to initiate a coloration process once the composition has transitioned to a solid crystalline form. It is also important that the coloration process is sensitive to the environmental temperature to which the crystalline composition is exposed to where the composition accelerates in coloration at increased temperatures and decelerates in coloration at reduced temperatures. Importantly, it is desirable for the colorization hue to change with absolute temperature that the composition is being exposed to. For example, an indicator can have a plurality of sensing applications if it both becomes colored with time and subsequently changes color from one hue to another depending on the absolute temperature of exposure.

Diacetylenic compositions have the advantage of coloration in the solid crystalline state through a topochemical polymerization reaction yet remaining stable and uncolored in a dissolved solution state. Diacetylenic monomeric materials can be made soluble in organic solvents. Solution-based diacetylenic monomers can form micro-crystalline films when deposited on a substrate. Application of monomeric solvent solution, containing a diacetylenic monomer, on a substrate leads to the rapid evaporation of the solvent carrier. The solvent evaporation process yields a micro-crystalline film of the diacetylenic monomer on the substrate.

The resulting micro-crystalline layer of the diacetylenic monomer on the substrate surface renders the monomer in a physical form capable of being cross linked through topochemical polymerization of the individual monomer molecules in the crystalline lattice. The diyne structure of one monomer can form a bond with an adjacent monomer through a 1, 4 addition. The reaction leads to a continued polymerization process which forms a conjugated ene-yne structure. The ene-yne structure is colored.

Diacetylenic materials in a crystalline state have the advantage of thermally annealing and polymerizing to form a colored entity. The degree of polymerization and subsequent color relates to the time and temperature the diacetylenic crystals are exposed to. Thermal polymerization in diacetylenic compositions to the colored polydiacetylenic form can be accomplished at a variety of relevant temperatures. The diacetylenic composition can be selected for thermal annealing and polymerization at below freezing temperatures, in the range of freezing temperatures, at common refrigerator temperatures (35° F.-55° F.), and above refrigerator temperatures.

For a given application, the molecular structure of a diacetylenic monomer will be selected based on how the structure will respond within the range of coloration intensities generated during the polymerization process, the time frame it takes for coloration to occur, the temperature at which the coloration is intended to occur and any intended pluralities of monitoring functions the intrinsic expiration initiation indicator is intended to have.

Diacetylenic monomers can be symmetric or asymmetric in structure. The key criteria for selecting a particular diacetylenic monomer as a plural intrinsic expiration initiation indicator is that it will become colored under the conditions and timing necessary to accurately profile the time and temperature exposure of interest. The monomer can come in the form of a straight chain aliphatic carbon chain, a single chain lipid, a symmetric bis compound, a dual chain molecule, a linear or branched compound, have aromatic or non-aromatic groups, have carbamate groups, carbonyl groups, ester linkages, amide linkages, polyethylene or polypropylene linkages, bridging groups, peptide linkages, azide linkages, thiol linkages, carbohydrate linkages, phosphate linkages or the like.

Thermochromically reversible compounds can be prepared by the addition of groups which strongly hydrogen bond intermolecularly. For example, amide linkages have the advantage of promoting stable crystal formation as well as strong intermolecular hydrogen bond formation which promotes thermochromic reversibility. Amide linkages on the monomeric compound assist in the preparation and utility of plural applications where it is important to measure both a time/temperature parameter for perishability through color generation as well as absolute temperature, both at low temperatures as well as reversibility to measure high temperatures.

Ester linkages promote irreversibility since esters do not significantly hydrogen bond. Non-hydrogen bonding systems have the advantage of irreversible coloration during the time/temperature monitoring process and subsequent irreversible coloration during a second plural monitoring event such as a higher temperature irreversible temperature triggering event.

Symmetric bis-alcoholic groups can be used to prepare plural intrinsic expiration indicators which become colored during the time/temperature monitoring process and subsequently can irreversibly change color from a blue color to a bright orange color either from complete hydration or exposure to temperatures above room temperature. For example, 4,6-deca-1,10 diol will thermally anneal at refrigerator temperature as a time/temperature indicator and irreversibly change color form a blue to orange color upon complete hydration.

Hydrocarbon chain lengths can be adjusted to expand plurality applications and to adjust the coloration process during time/temperature monitoring. For example, short chain compounds including 5,7-dodecadiynoic acid, 5,7-tetradecadiynoic acid, or 5,7-hexadecadiynoic acid may be used without further modification or be further modified. In either case, the low melting transitions of these compounds permit activation at low temperature in a crystalline state whereas maintaining these compounds above their melting transition state prevents crystallization and therefore prevents thermal polymerization. Modification of these compounds to amide forms can both promote thermochromic reversibility and increase the melting transition.

Longer chain compounds with chain lengths from 18 carbons to 30 carbons can significantly increase the melting transition of the plural intrinsic expiration indicator and thereby be applied to a combination of time/temperature indication and plural applications such as color changes indicating safe cooking temperatures.

Medium chain length carboxylic acid derivatives such as 10,12 tricosadiynoic acid and 10,12-pentacosadiynoic acid used as plural intrinsic expiration indicating materials have the combined property of becoming colored with time and temperature, but at a dramatically reduced rate. Therefore, compounds such as these have the advantage of serving as long term monitoring materials. For example, they may become colored over periods of weeks or months rather than days. In addition, compounds such as these will change color thermochromically at different elevated temperatures depending on the degree of polymerization achieved. Low levels of polymerization and coloration will result in compositions which turn from a blue form to a red form at temperatures in the range of 100° F. to 130° F. Increasing levels of polymerization lead to a thermochromic color tradition of between 130° F. and 150° F. Yet higher levels of polymerization to a dark black blue hue can lead to a thermochromic color tradition above 150° F. Compositions such as 10,12 tricosadiynoic acid and 10,12-pentacosadiynoic acid provide for the development of plural intrinsic expiration indicating devices which measure time and temperature and subsequently indicate increasing temperature exposure levels for cooking or preparation.

Chemical Doping and Initiation Enhancers

Diacetylenic monomers of a specific chemistry can be doped with trace amounts of a similar co-crystallizing diacetylenic monomer. The process of doping trace amounts of a compound can effect the time/temperature sensitivity of the final composition. For example, trace amounts of a doping agent in the range of 1-10% of an 18 carbon chain diacetylenic compound can be admixed into a pure composition of a 16 carbon chain diacetylenic compound. The doping process can provide defect structures within the final crystal matrix. Defect structures can facilitate polymer formation by providing flexibility within the crystal lattice. A resulting admixed or doped crystal may more rapidly or more sensitively crystallize compared to an undoped crystal lattice.

Doping compounds can be added to a pure diacetylenic composition from 50% to 0.001% by weight. Usually, doping compounds are added from between 25% to 0.01% and more usually between 15% and 0.1%. Typically doping compounds are added between 10% and 1% by weight. The doping compound added will depend on the monomeric diacetylenic compound selected as the plural intrinsic expiration indicating molecule.

Usually the doping compound or agent will itself be a similar diacetylenic compound, however may also be a compatible organic compound which may effect the formation and sensitivity of the resulting polydiacetylenic polymerization reaction. Usually the doping compound will differ from the dominant monomer by not more then 10 carbon atoms. More usually the doping compound will differ from the dominant monomer by not more than 5 carbon atoms and typically by only 2' carbon atoms. For example, 10,12-pentacosa diynoic acid can be doped into a pure formulation of 10,12-tricosa-diynoic acid to enhance its sensitivity to thermal annealing.

Doping compounds can be added to the final plural intrinsic indicating composition at any of a number of steps or elements of the indicating device. The doping material may be added into the carrier solvent to be applied to a substrate. The doping material may be impregnated into the substrate itself during the processing and preparation of the substrate. Alternatively, the doping material may be added to an ink composition used for coloration of the background at the location where the intrinsic expiration indication material is intended to be applied.

Promotion of the initiation process also can be accomplished by physical and chemical means which may be used to enhance the time temperature coloration process. Sensitizing chemicals, polymerization enhancers, and inducing agents can be employed to impact the coloration process. Enhancers or modulators can be used to speed up the coloration process or slow down the process. For example, low levels of light may be employed to modulate or accelerate the coloration process. Although the coloration process can take place in the absence of external light induced polymerization in monomer crystals, the presence of low levels of ultraviolet light (254 nm peak bandwidth) can significantly accelerate the coloration time and dramatically reduce the time frame for monitoring a particular perishable object.

Metal salt forms of plural intrinsic expiration indicating materials in monomeric forms can be utilized to modulate sensitivity. Compatible counter ions to carboxylic acids or amines can be used to sensitize or desensitize the completion to coloration over a time and temperature profile exposure. For example, cadmium, calcium, sodium or other ions can be used to form salts. Other metals can be used to participate in the polymerization process as augmentors such as platinum or other rare or common metals. Pure or mixed metals can also be used.

Carrier Solvents

Solvents used for solubilizing, dispersing, spreading and evaporating to leave behind the monomer as a plural intrinsic expiration indication material are selected based on their effectiveness at forming a final monomer micro-crystalline film. The choice of solvents can effect the type of monomer crystals formed, the crystal integrity and polymerizability of the monomeric material.

Certain solvents promote rapid dispersive crystallization of the monomer and yield an application mark which is active within the desirable range of time/temperature indication intended. For example, ethanol and chloroform solvents either alone or in mixtures serve as compatible solvents. Methanol and acetone tend to be poor spreading solvents since monomeric diacetylenic compounds tend to form poor crystals upon solvent evaporation.

Volatile solvents which can be used to dissolve and disperse the monomer onto a substrate include: ethanol, chloroform, dichloromethane, carbon tetrachloride, terpenes, ethers, propanes, ethyl acetate, hexane, hexanes, acetonitrile, combinations of solvents, benzene, isopropanol; methanol, butane, isobutanol, glycol, methylethylketone, low temperature polyethylene glycols, polar and apolar solvents, and the like.

Combinations of solvents may be used to modulate the solvent evaporation process. Solvents in which the monomer is highly soluble may be used in mixtures with solvents in which the monomer is less soluble. A balance of solvent concentrations may be used where the evaporation rate of the highly soluble solvent exceeds the evaporation rate of a less soluble solvent. The concentration balance changes between the different solvents can be used to influence the monomer crystallization process during application of an ink to a substrate. Mixed solvent systems can be used to increase or decrease sensitivity of the plural intrinsic expiration initiation indication system.

Carrier Ink Compositions

Carrier ink compositions include a solvent for solvating and solubilizing the monomer and a concentration of the monomer practical for application to a substrate. Generally, concentrations of monomer range from 500 mg/ml to 10 mg/ml, more usually from 300 mg/ml to 25 mg/ml, and typically from 200 to 50 mg/ml.

High monomer concentrations can be used to increase the rapidity of color development and shorten the time exposure profile. Low monomer concentrations can be used to increase the time for color development and prolong the exposure profile. The concentration of the plural intrinsic expiration initiation indicating material can be adjusted in combination with the substrate porosity and background stationary ink to calibrate the intended time/temperature profile intended for a particular perishable application.

Carrier ink compositions can be formulated to include inactive agents such as thickening materials, coating materials, protective materials and the like. The type and grade of additional inactive agents selected will depend on the particular need required by a product application. For example, for extremely high sensitivity applications where it is important for the intrinsic indicating material to become colored within a short period of time, a thickening agent may be desirable to include since the thickening agent can facilitate the application of thick layers of the intrinsic indicating monomer. The thickening agent promotes increase concentrations of monomer to be applied, thereby increasing the color appearance during a shorter time frame.

Inactive agents are generally added at concentrations where they are of use. The inactive agent concentration generally ranges from 1000 mg/ml to 0.1 mg/ml, more usually from 500 mg/ml to 1 mg/ml, usually from 250 mg/ml to 5 mg/ml and typically from 200 mg/ml: to 10 mg/ml. It is particularly important to select a thickening agent which does not interfere with the physical and chemical properties of the plural intrinsic expiration initiation monomer, its crystallization properties, or polymer formation from the diacetylenic monomer to polydiacetylenic polymer.

Examples of inactive agents include polyethylene glycols, polypropylene glycols, carbohydrates, cellulosic materials such as nitrocellulose and methyl cellulose, inert plastics such as acrylics, styrenes, methacrylates or the like, micro-plastic beads used for gel and ball point inks, emulsifiers such a lecithin, lipids and polymeric lipids and other inactive agents typically used as thickening agents.

Application Substrate Surface Characteristics

The monomer solution can be applied to any of a variety of surfaces. The surface should be clean, uniform, have a coloration which provides contrast compared with deposited monomer that converts to a colored time/temperature indicating polymer, and should be free of any components which could negatively impact the monomer from forming a micro-crystalline coating or from converting to a colored polymer under the conditions intended for time/temperature indication.

More porous surfaces have the advantage of accumulating larger amounts of monomer solution whereas less porous surfaces may accept smaller amounts of monomer solution during the application process. Various substrates may be treated in a particular way either chemically or physically to be more or less porous. For example, papers can, be made with an open fiber to increase porosity whereas they can be treated with a varnish to reduce porosity. Plastics can be plasma irradiated to increase porosity or heat treated and annealed to reduce porosity. Metals may be chemically etched to increase porosity and polished to reduce porosity. The degree to which a substrate is treated to increase or decrease porosity will depend on the application of interest and the intended sensitivity of the plural intrinsic expiration initiation indicator.

Substrate surfaces utilized for spreading the monomer solution on are selected based upon their properties for final monomer micro-crystal formation. The surface should assist in the, uniform formation of micro-crystallization of the monomer. Porous surfaces attract increasing levels of monomer solution thereby compartmentalizing more monomer per cross-sectional area.

Application Substrates

A wide range of substrates for application of the intrinsic indicating material can be employed. The substrate type selected will depend on the implementation and specific product embodiment utilized for the intrinsic indicating material. Substrates may be used as an attachment to a food container or the container itself. The container may be single-use such as a bag or multi-use such as a plastic container or storage pan. An attachment substrate can be an adhesive, label or other item which can be put in contact with a food storage container.

The substrate may be flexible or rigid depending on the intended application. The substrate may also be permanent or disposable immediately after use. For example, it may be desirable for certain applications that the substrate be permanently affixed to a container and the substrate be used repeatedly with the same plural intrinsic expiration initiation marker. Alternatively, it may be desirable for other applications that the substrate be single used and disposable where the substrate is affixed to a single use container such as a deli dish.

Substrates are selected for their ability to beneficially interact with the intrinsic indicating material, its compatibility with food storage conditions, its compatibility with a food storage container and other properties such as visibility, opacity and porosity amenable to visualizing the color development of the intrinsic indication material.

Substrate material compositions can include, but are not limited to, papers, cardboard, plastics, metals, alloys, glass, wood, ceramics, printed inks, paint, foils, extruded surfaces, wax, carbohydrate material, cellulosic material, sintered surfaces, lacquers, cloth, adhesives materials, glues, epoxy resins, polymer resins, heat sink materials, solder, thermoforming materials, medical substrates, rubber, vinyl materials, silicon rubber compounds, various polymer based composites, and a variety of other compatible materials which can serve as suitable substrates or matrices for the plural intrinsic expiration initiation indicating materials.

Substrates can be rigid or flexible depending on the intended application of interest. For example, a flexible substrate such as painted surface has application to a storage bag where the perishable food is stored. A rigid substrate has application to a rigid storage container where the storage container has a compartment for inserting a plastic tab where the plastic tab is the rigid substrate for applying the intrinsic indication material.

The substrate can also be a liquid where the intrinsic indicating material is admixed from a solubilizing solution and precipitated or micro-crystallized with a precipitating solvent. Blending of the soluble solution containing the monomer with the precipitating solvent at time zero will cause an immediate precipitation or crystallizing process and initiate the time/temperature indicating process.

Substrates and/or items to be marked with the intrinsic indicating material include but are not limited to: label material which dissolves in water such as that sold by DayMark Food Safety Systems Inc. under the trademark DISSOLVE-A-WAY®, standard printable commercially available label materials such as paper and plastic, plastic tapes, paper tapes, cloth tapes, freezer tapes, transparent films, paper tags, name tags, clips with name tags, aluminum foil, shrink wrap material, plastic bags, printed plastic bags, sintered surfaces, standard and treated paper, plastic card stock, miscible solvents such as water, cotton cloth, various textile fabrics, mesh materials, wrapping films, butcher paper, butcher tapes and, sealing materials, printed ink labels, painted zone, pressure sensitive strips, rubber bands, heat sink materials, packaging material, plastic pans, metal pans, glass dishes, paper boxes including cardboard boxes, bandages, Tyek brand extruded packaging material, wood implements, cheese cloth, medical substrates including medical diagnostic paper test strips, tracing paper, acetate surfaces, plain colored paper Post-it brand notes (3M Company), plain and colored Post-it brand plastic Flags (3M Company), tape tabs and the like.

Substrate Additives

Substrates can also be formulated with added nucleation sites to enhance the micro-crystal nucleation process. Adding micro-crystal nucleator materials has the added benefit of overcoming inconsistencies in a normally non-uniform substrate. Good nucleating materials can be insoluble in the solvent used to carry the monomeric indicating material.

Nucleating materials include micro-particulate powders such as silicones, talc powders, fine grain fibers, dye powders including raw colorants for plastics and papers, filtration materials such as chromatography materials, organic and inorganic materials, mineral powders, titanium dioxide powder, starch powders, ceramic powders, insoluble clear plastic resin powders, polyethylene glycols, polypropylene glycols and the like. Alternatively, the nucleation material can be added at final concentration relative to the carrier solvent employed. Generally, concentrations of nucleating enhancer can range from 1000 mg/ml to 1 mg/ml, usually from 500 mg/ml to 5 mg/ml, and typically from 250 to 10 mg/ml and more usually from 100 to 25 mg/ml.

The nucleating material can be added directly to the substrate during substrate formulation or can be added to the carrier solvent and monomer composition and delivered to the substrate during the, process of marking the indication material to the substrate.

The nucleating material can be imprinted on a substrate as a part of the imprinting process used to create a background color on the substrate of interest. For example, the nucleation material can be formulated with an ink which is used to create a background reference color.

Contrast Colors and Backgrounds

Stationary non-changing colors can be added to the solvent carrying the initiation monomer. The color serves the purpose of indicating where the initiation monomer is being applied. Additional colors may also be used to reduce the risk of misinterpretation in the event that the initiation monomer pen is dry at the time of use. The presence of a stationary color will help the user identify that the pen is working properly. The hue, intensity, contrast or other printing parameters can be adjusted to calibrate the intended contrast of the color developed by the intrinsic expiration indication material.

Background stationary color hues can be adjusted to prolong the apparent color development of the plural intrinsic expiration indicator. For example, if the plural intrinsic expiration indicating material becomes dark purple-blue at refrigerator temperatures, backgrounds with reds, magentas, purple, and blues tend to blend in with the indicator and prolong the apparent time to expiration. Backgrounds with yellow and green hues tend to provide higher contrast in combination with a blue-tinted indicating material tending to reduce the apparent time to expiration.

Background stationary colors can be any compatible or complimentary color with the color change produced from the intrinsic indicating material. Colored backgrounds can be created using standard printing methods such as off-set, ink jet, rotary letter press, flexography, pad printing, spraying, photographic, thermal imprinting, and any variety of printing processes which yield a surface compatible with the deposition and activity of the intrinsic indicating material.

Pre-colored/polymerized plural intrinsic expiration indicating materials can be pre-coated on a substrate and serve as the reference background for marking with a solvent soluble monomeric intrinsic indicator. This process has the advantage that the solvent in the application device can immediately trigger a color change in the pre-colored/polymerized background indicating that the application device is charged with the solvent solution and is not dried out. In addition, the solvent/monomer solution delivered to the substrate surface will be easily located on the background by triggered mark. As the time/temperature process ensues, the expiration indication can be visualized by a color change in the mark. The mark will change color over time and depending on temperature to become the same color as the original background pre-colored/polymer. The background color can be calibrated and used as a reference color for indicating what the final color of the indicator should be in order to indicate when an attached item is perished.

Printing methods can be used to encode reference colors which provide a reference coloration as to subsequent environmental exposure conditions that may be indicated by the plural intrinsic expiration application device. For example, where colored backgrounds may be used to enhance the contrast of the color development process that the plural indicator generates during a time/temperature profile, stationary printed colors such as a orange/yellow can be pre-printed in a location as to provide a color reference as to what the final color will be if the indicating material is heated to a selected temperature for cooking as an example.

Printing processes and commercial printing inks can be further utilized in combination with porous substrates to regulate the permeability of the porous substrate and provide a color contrast to the final coloration of the plural intrinsic expiration initiation material as the color develops during an application. Dot gain, dot size, dot shape, dot coloration, and percent coverage of a pre-printed area can be used to regulate the amount of plural intrinsic expiration initiation material delivered to the porous substrate.

Commercial printing inks can be highly, impermeable, moderately permeable, or permeable to the plural intrinsic expiration initiation ink. Impermeable commercial printing inks can be used in formats where the printed zone or area resists permeation of the plural intrinsic expiration initiation ink. For example, dot patterns in various percent coverage can be used to adjust the permeation of the plural intrinsic expiration initiation material. During application of the plural intrinsic expiration initiation ink, the ink will be absorbed into a porous substrate and incorporated around the ink zone. The ink zone can act as a barrier region where on the surface little or no ink will deposit. The pre-printed ink zones can serve to effectively concentrate the plural intrinsic expiration initiation material in the porous areas between the pre-printed zones. In addition, the coloration of the pre-printed area can be adjusted to match or contrast the final coloration of the plural intrinsic expiration initiation material.

Pre-printed regions can have coverages from 0.1% to 100%. More usually pre-printed coverage will range from 0.5% to 90%. Typically coverage will range from 1% to 70%. The range of coverage will depend on the perishable application of interest. The printed dot size can range from 0.001 millimeter to 1 millimeter and typically from 0.01 millimeter to 0.1 millimeter. Multiple side-by-side printed zones with pre-adjusted percent coverages find use in applications where the plural intrinsic expiration initiation device can have multiple choices of expiration periods.

The side-by-side format permits the selection of a particular expiration period. For example, 7 zones each representing 7 sequential days of a calendar week can be printed with varying percentages of pre-printed impermeable ink. The ink hue can match the final coloration of native plural intrinsic expiration initiation material during coloration. When a particular weekday is marked for anticipated expiration with an ink containing the plural intrinsic expiration initiation material, coloration will proceed such that the region marked will accurately indicate expiration on the anticipated day.

Application Delivery Systems

A wide range of application delivery systems may be used for applying the solvent solubilized monomeric solution depending on the amenable application process. Application delivery process can utilize a simple manual process such as a felt tip pen filled with a soluble ink composition containing the monomeric plural intrinsic initiation indicating material for marking. Alternatively, an electronic applicator device can be employed which has a reservoir of ink and prints the ink automatically on dispensed labels or bags on demand. In each case, the printing or application process initiates the time/temperature measurement process since the process requires solvent application of the monomer to a substrate.

Delivery processes can include: in-line printers, piezo-electric ink jet printers, bubble jet printers, commercial ink jet printers, off-set printers, flexographic printers, drum printers, pad printers, ink pads, markers, stamps, stampers, compartmentalized solvent water systems, felt tips, sponge, adhesive removal, dissolve, liquid dispensers, finger paints, self inking stamp, rubber stamp, wipe-ons, pans, pencils, crayons, ball point pens, electronic stampers, scratch-off for release, liquid gel caps, stencil applicators, balm applicators, liquid tube applicators, spray ons, roll ons, rub ons and the like.

Containers with Foods/Beverages

Food and other perishable products may be stored at refrigerator temperature in any of a variety of containers suitable for a particular organization. Plural intrinsic expiration initiation indicators can be applied to a container in a form or format compatible with the container. For surfaces on a reusable container, it is desirable to use an indicator which can be applied for monitoring during a particular period. Labels are desirable since they can be applied directly to a pan, tub, box or other compatible surface for usage during a specified period.

Containers can include: boxes, pans, tubs, plastic bags sacks, jars, cans, paper wraps (meat paper/butcher paper), milk bottles, blood bags, racks, drums, cartons such as egg cartons, hermetically-sealed bags, liquid dispensers, packets, pouches, envelopes, vegetable bags, storage containers, tags, hock locks, tape, thermoses, sperm bank containers, tubes, pharmaceutical drug containers wire labels, aluminum foil wraps, plastic wraps, styrofoam trays, and canisters or the like.

In particular, a variety of different plastic bag materials, compositions, shapes, colors, designs or the like can be used as storage containers for perishables and are compatible with plural intrinsic expiration indicators. Bags can be used for a singular purpose such as storage of specific food proportions. Storage bags are typically made with polyethylene or polypropylene. Bags can be used for multiple purposes such as storage and cooking. For example, polyester and nylon bags can be used to both store meat and withstand the temperatures necessary for cooking.

Bags can be imprinted with a fluid ink where the imprint can serve as the substrate for marking with the plural intrinsic expiration indicator. Alternatively, a label pre-printed with appropriate graphics, may be adhered to the bag and used as the substrate for applying the plural intrinsic expiration indicator. In either case, plastic bags serve as an attractive disposable container for utilizing an application form of the plural intrinsic expiration indicator.

For containers that will be washed subsequent to the food storage period, it is desirable to use plural intrinsic expiration initiation indicator as the substrate for the labels which dissolve in water and/or detergent or soap such as the previously reference DISSOLVE-A-WAY® labels. Labels which dissolve permit the easy application of the indicator to a container and easy removal of the label during the cleansing process for cleaning the container.

Visual Output

The visual output resulting from the color formation caused by the plural intrinsic expiration initiation indicator can range from a simple mark or line to a more complex message or graphic. For example, a simple mark, check or strike can be made using a felt tip pen as the delivery method for applying the material. A mark can be combined with a stationary visual graphic printed on the intended substrate. For example a partial warning sign can be graphically printed on a substrate using a contrast ink base. The intrinsic expiration initiation indicating material can be marked on the graphic in such a manner as to complete the visual graphic once the indicating material has changed color.

As an illustration, a printed color circle with a round darkened border can serve as the initial graphic. The intrinsic material can be marked diagonally across the center of the circle. After color generation from the intrinsic material, the final resulting graphic intended to indicate expiration can show a round circle with a line through it. A "cross-through" circle has the generic connotation that something should not be used or should not be handled. Combining symbolism with the use of the plural intrinsic expiration indicator has the advantage of reinforcing that a particular item has perished and should no longer be used.

A variety of other symbolic means, messages or the like can be utilized including: the integration of bar codes, graphics, numbers, letter words, marks, lines, visuals, pictures, stamp imprints, line art, graphic compilations, symbols, warning emblems, holographic diagram, block diagrams, dock, fluorescence output, black light patterns, fill-in/threshold diagram, obscuring message, revealing message, grids, lines, patterns, textures as well as a variety of other graphic means.

Applications

The plural intrinsic expiration initiation indicator can be used in food service, restaurant, hospital, blood banking, shipping and distribution, recreational and outdoors activities, theme parks, fairs, school lunch programs, commercial, institutional, medical, consumer home-use, educational, industrial, agricultural, dairy, and other relevant areas of applications where a product or item of interest should be periodically monitored for expiration. Perishable items and items which change their characteristics over time may be monitored using the indicator.

Specific examples of perishable products which should be periodically monitored and have utility for plural intrinsic expiration initiation indicators include: foods including raw meats, mail and email order meats and perishables, raw poultry, bulk uncooked hamburger and hamburger patties, raw fish, sausage, once cooked items, lunch meats, cheese, children's consumables such as Lunchables (Kraft Corp.), consumer home use repackaged perishables such as hot dogs, fast food served, Chinese food, Mexican food, sushi, cookie dough, perishable liquid beverages such as milk and cream, coffee, butter, condiments, wines, beverages, fresh and frozen foods, ice cream, raw cookie dough, thawed foods such as previously frozen pancakes or waffles, tofu, eggs, photographic films and papers, cigars, cosmetics, pharmaceutical and medicinal products, stored blood, sperm in sperm banks, stem cells, fertile and non-fertile eggs, tissues in hospitals or tissue banks, tissue cultures, bacterial cultures, DNA samples, transplantation organs, sensitive chemicals, fine reagents, airline service foods, leftovers, baby formulas, stored mothers milk, post sterilized products, diagnostic devices, perishable products with broken seals, materials with half-lives, agricultural products such as seeds, germ cells, light sensitive materials, toxic perishable waste in urgent need of treatment; compositions which may undergo flavor loss, home-use water filter exchange, and the like.

Plurality Applications (Permutations)

The plural intrinsic initiating expiration initiation indicator can be used in a singular format to report one element of an expiration process or be used in a tandem fashion where the indicator reports or monitors the progress of one or more processes. The indicating mechanism, composition, substrate, formulation, algorithm and other ancillary qualities can be adjusted according to the type of application the indicator is intended to be used for.

A continuum of application for a particular plural intrinsic initiation expiration indicator can be accomplished by selecting a composition which undergoes multiple color change events. Plural intrinsic indicators provide for more than one sequential or simultaneous indications arising from of a single detection device. For example, an indicator can be used to monitor the perishability of foods by indicating a color formation over time and temperature while simultaneously indicating the absolute temperature of the environment that the food has been raised or lowered by the color hue that the indicator changes to.

In another example, a plural indicator can monitor perishability of foods by indicating a color formation over time and temperature while also indicating the degree of humidity that the indicator is exposed to. Thermally polymerizable material compositions of diacetlyenic monomer can be employed that develop color with time and temperature and subsequently change to another color upon hydration due to humidity or exposure to bulk water.

A variety of singular through plural indication parameters can be simultaneously or sequentially monitored using a plural intrinsic expiration initiation monitor including examples such as: time-reduced temperatures, time-varying temperatures, time-elevated temperatures, time/temperature storage combined with subsequent hot holding temperature, time/temperature storage combined with subsequent cooking temperature, time/temperature storage combined with subsequent sterilization temperature, time/temperature storage combined with subsequent cooking temperature combined with further subsequent post-cooking storage, short time/temperature combined with ultraviolet irradiation sterilization, long time/temperature combined with dishwasher safety temperature achievement, time/temperature storage combined with irreversible elevated temperature monitoring, high temperature storage maintenance combined with revisable temperature cooling, prolonged ultra-low temperature storage combined with short time elevated temperature exposure, time/temperature storage combined with humidity exposure at elevated temperatures, time/temperature storage combined with hydration submersion, and a variety of other time, temperature, temperature cycling, irradiation, hydration, and other environmental exposure conditions and the like.

EXAMPLES

Solvent based ink formulation: An ethanol/dicholormethane ink formulation was prepared using a solvent composition containing absolute ethanol. (Aldrich Chemicals) to dichloromethane (Aldrich Chemicals) 5 to 1 by volume. N-ethanol-hexadeca-5,7-diyneamide. (prepared synthetically) was dissolved in ethanol to dichloromethane 5 to 1 by volume and filtered through filter paper using gravity filtration (Whatman no. 541) to a final concentration of 200 mg/ml. The final solvent based ink formulation was clear and free of any particulate matter. The ink base was tested for its color changing characteristics by application to paper and plastic surfaces. Ink marks, once dried, were exposed to ultraviolet light (254 nm) for several seconds using a hand held lamp. The ink marks immediately turned a deep magenta color at room temperature. The ink base was used in filling a variety of printing devices including pens, ink jet cartridges, stamps and the like.

Plural intrinsic expiration indicator felt tip ink pen applicator: A monomer felt tip ink pen applicator was prepared using the solvent base ink formulation above. An empty felt tip pen body (DriMark Inc.) was filled using 200 mg/ml of the solvent ink formulation previously described. The ink formulation was stable at room temperature when stored in the felt tip ink body. The pen was tested for writing on a variety of paper, plastic, printed, painted, metal, and other substrate surfaces. In each case, the substrates were tested for their porosity and contrast for color development. Surfaces were compared for ink polymerization activity using exposure with ultraviolet light (254 nm) for several seconds using a hand held lamp. More porous surfaces such as papers showed a high level of color formation, whereas less porous surfaces such as metals and plastics showed less color development.

Plural intrinsic expiration indicator felt tip ink pen applicator encoded with a stationary color background yellow: A monomer felt tip ink pen applicator was prepared using the solvent base ink formulation above. An empty felt tip pen body (DriMark Inc.) was filled using 200 mg/ml of the solvent ink formulation previously described. The ink formulation was tinted yellow with a solvent based yellow ink. The yellow ink was added to be used as a permanent yellow additive at a concentration of 1 ml permanent yellow ink (Pantone yellow, Letraset, England) to 10 ml solvent ink formulation in order to indicate where the plural intrinsic expiration indicating material was being applied. The ink formulation was stable at room temperature when stored in the felt tip ink body. The pen was tested for writing on a variety of paper, plastic, printed, painted, metal, and other substrate surfaces. In each case, the substrates were tested for their porosity and contrast for color development. Surfaces were compared for ink polymerization activity using exposure with ultraviolet light. (254 nm) for several seconds using a hand held lamp. More porous surfaces such as papers showed a high level of color formation whereas less porous surfaces such as metals and plastics showed less color development.

The yellow additive had the advantage of indicating where the plural intrinsic expiration initiation indication mark was placed and if the ink pen dried out after prolonged use. The yellow additive caused a yellow mark to turn green at refrigerator temperature's in combination with blue color development of the plural intrinsic expiration initiation material.

Printed DISSOLVE-A-WAY® labels for plural time/temperature and temperature monitoring devices: 2 inch by 3 inch die cut DISSOLVE-A-WAY® labels were printed with visual graphics using an ink jet printing system (Epson Stylus Color 3000, Epson Inc.). Instructional information, naming information, graphic display and background coloration (blue hues) were printed within the label border. 5 side-by-side circles (0.5 inch dia.) each with a circular outline were displayed from, clear background on the left with progressively increasing blue tinted centers moving to the right hand circle. The circles were numbered 1 through 5 indicating which day from marking the label would indicate expiration. The label also contained a graphic reference as to what a user sees when label indicates expiration.

For use, the label was applied to a plastic pan containing perishable uncooked chicken pieces. The contents were expected to expire 3 days after purchase. The label was placed in a visible location on the side of the pan. The third day (day 3) circle was marked diagonally with the monomer felt tip ink pen applicator containing the plural intrinsic initiation expiration indicator (see example above "Plural intrinsic expiration indicator felt tip ink pen applicator"). The mark was placed in the circle in direction consistent with the reference graphic. The pan was placed, in a refrigerator and stored at 40° F. for several days. The refrigerator was opened and closed under a standard routine of use. The pan was removed from the refrigerator 2 times per day on day 1, 2, and 3 for 5 minutes per time. The diagonal mark through the day 3 circle became visible on the third day from application indicating that the pan contents had expired. The indicator mark also transitioned from a light blue hue to a magenta hue once the pan had warmed to room temperature further indicating that the contents had not only expired, but also were further perished by exposure and equilibration to room temperature.

The pan contents were disposed once the indicator registered expiration on day 3 from initiation. The pan was washed using a conventional dishwasher during which time the DISSOLVE-A-WAY® label was dissolved as intended. All inks, the plural intrinsic initiation expiration indicating material, and adhesives were effectively removed and eliminated as intended during the washing process leaving behind a clean pan for subsequent usage.

Figure 1B:
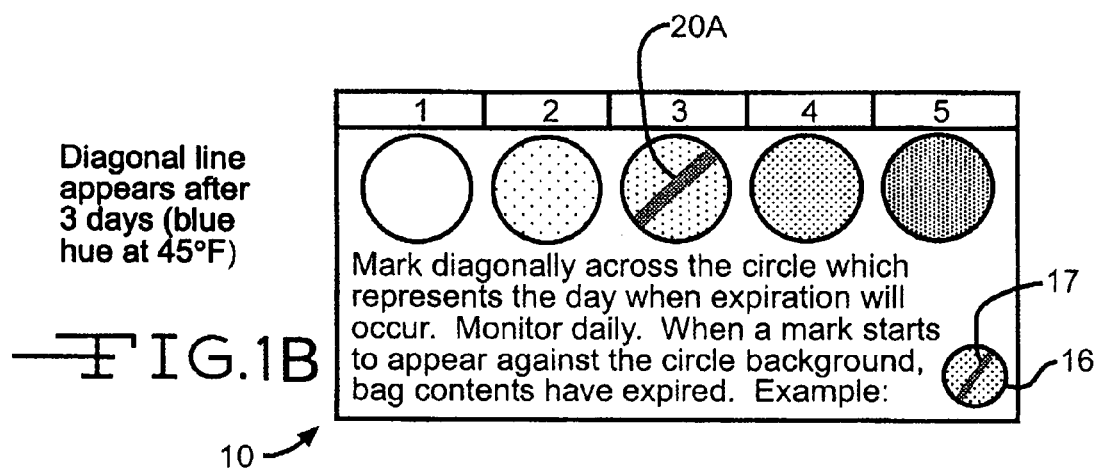
FIG. 1B shows the label of FIG. 1A after three days when the food has expired.
Figure 1C:
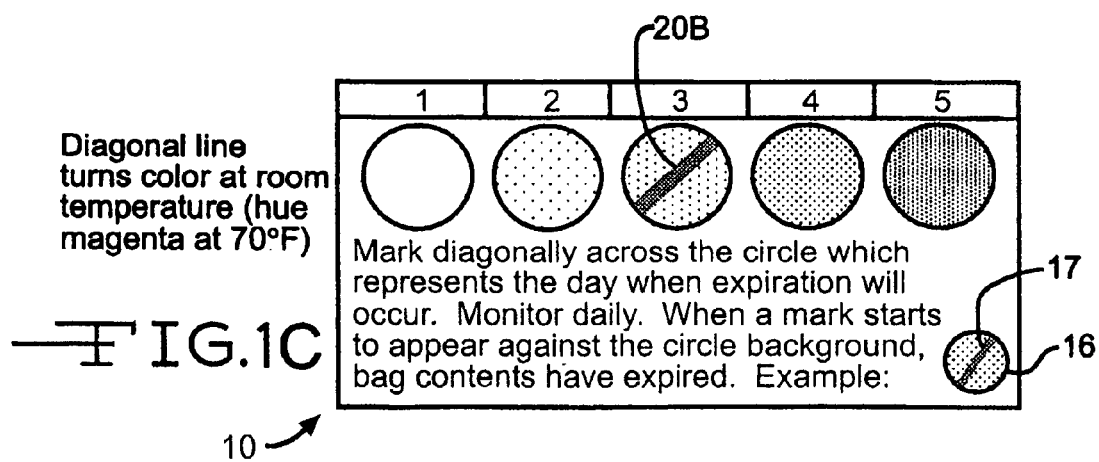
FIG. 1C shows the label of FIG. 1A indicating that the food has expired after three days and has further perished by exposure and equilibrium to room temperature.

Referring to FIGS. 1A, 1B and 1C, there is shown a label generally designated by the numeral 10. The label 10 may be paper, a water dissolvable material such as that sold by the Assignee of the present patent application under the mark DISSOLVE-A-WAY® and described in U.S. patent application Ser. No. 10/008,911 filed. Dec. 6, 2001 or any of a number of plastics used as label materials such as low or high density polyethylene, VPC or PET. The label 10 had printed thereon five side-by-side circles, 11, 12, 13, 14 and 15 with a number printed above each circle, namely, the number 1 appearing above circle 11, the number 2 appearing above circle 12, the number 3 appearing above the circle 13, the number 4 appearing above the circle 14 and the number 5 appearing above the circle 15. Displayed within the circular outline of circles 12, 13, 14 and 15 was a background coloration in a blue hue or tint with increasing degrees of tinting from a faint tinting in circle 12 and progressively greater tinting in circle 13, more in circle 14 and the greatest degree of tinting in circle 15 as represented by the increasingly darker indications as indicated in FIGS. 1A, 1B and 1C. Circle 11 was displayed with a clear background.

Below the circles 1-5 is printing showing instructions to the user to make a diagonal line 20 with the felt tip ink pen applicator containing the plural intrinsic initiation expiration indicator monitor. The diagonal line is to be made through only one of the circles, namely, that circle which represents the day when expiration of the food or other expiration-sensitive goods should be removed from service if not consumed or used prior to such day. In FIG. 1A, the food contained in a container to which the label 10 was attached was of a type which was generally recognized to have an expiration of three days from the date of receipt at a restaurant or other consumer when stored in a refrigerator at temperatures on the order of 45° F. Accordingly, circle 13 was marked with a felt tip ink pen applicator containing a clear intrinsic initiation expiration indicator of the type previously described, for example, an ethanol/dicholormethane monomer. Since the monomer was clear, the mark in FIG. 1A extending diagonally in circle 13 has been shown with dashed lines identified by the numeral 20.

If desired, a yellow additive may be incorporated into the monomer which, when applied to a circle having a blue tinted center will be visible as a green color. The use of the yellow additive will clearly confirm to the user that circle 13 of label 10 has been marked with a pen containing the plural intrinsic initiation expiration indicator monomer.

In the lower right of the label 10 is another circle 16 smaller than the circles 1-5 and containing therein a diagonal line 17 in a permanent, unchanging color indicating the color to which the diagonal line 20 of FIG. 1A will appear when the food has expired. In the example shown, the diagonal line has turned to a blue hue after storage of three days at a nominal temperature of 40°-45° F., being approximately the temperature of the non-freezer portion of refrigerators. The blue hue is represented by the numeral 20A in FIG. 1B.

FIG. 1C is a representation in which the diagonal line formed by the felt tip pen using the plural intrinsic initiation expiration indicator monitor has changed to yet a different color, namely, magenta, after the goods which had been removed from the refrigerator after three days and then left at room temperature of approximately 70° F. The change in color to magenta as indicated by the diagonal line 20B was an indication that the goods had further perished by exposure and equilibrium to room temperature.

Plurality device for time/temperature and 160° F. irreversible color change indicating subsequent cooking completion: Printed labels were prepared to monitor and indicate both food product expiration and cooking. Printed labels were prepared similar as above. 2 inch by 3 inch die cut labels were printed with visual graphics using an ink jet printing system (Epson. Stylus Color 3000, Epson Inc.). Instructional information, naming information, graphic display and background coloration (blue hues) were printed within the label border. 5 side-by-side circles (0.5 inch dia.) each with a circular outline (0.1 inch perimeter) were displayed from clear background on the left with progressively increasing blue tinted centers moving to the right hand circle. The circles were numbered 1 through 5 indicating which day from marking the label would indicate expiration.

The label was modified with a pre-printed square containing a pre-polymerized zone with the polydiacetylenic polymer of N-ethanol-hexadeca-5,7-diyneamide (prepared synthetically). The pre-printed square turned blue when cold, magenta at room temperature, and irreversibly orange when elevated above 160° F. The pre-printed region contained the same material as the material used as the plural intrinsic initiation expiration indicating material.

Figure 2A:
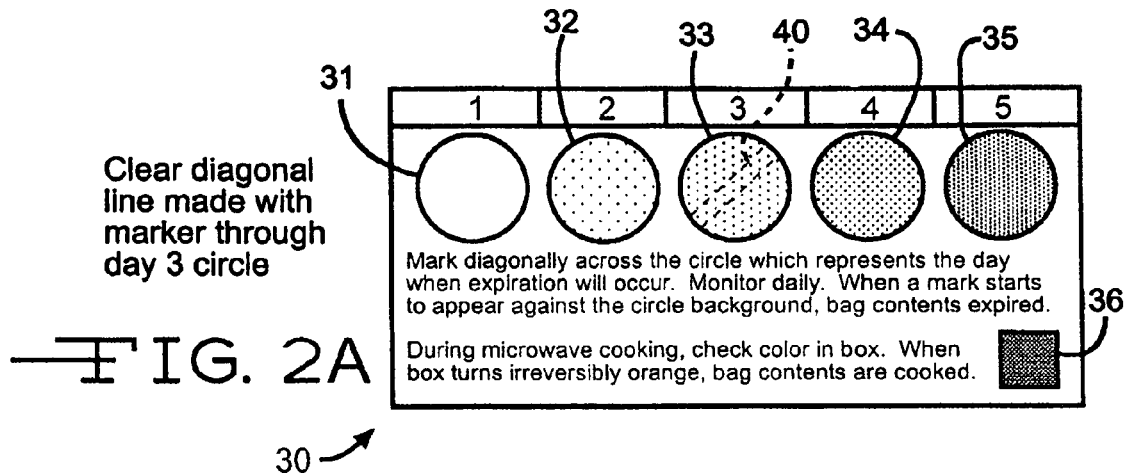
FIGS. 2A-2C show labels of the present invention, as described in FIGS. 1A-1C, which designates the monitoring and indication of both food product expiration and cooking.
Figure 2B:
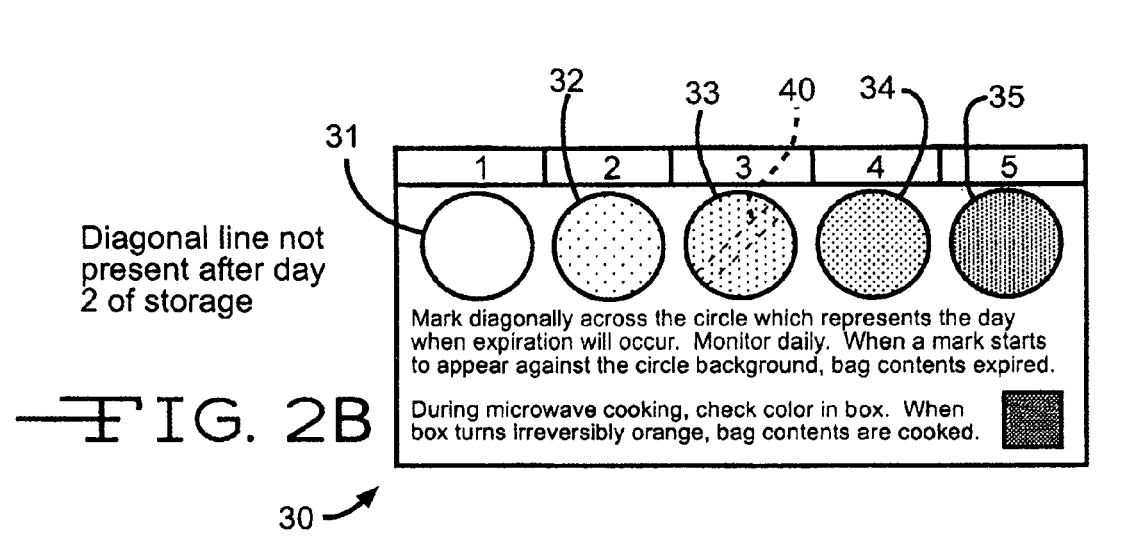
Figure 2C:
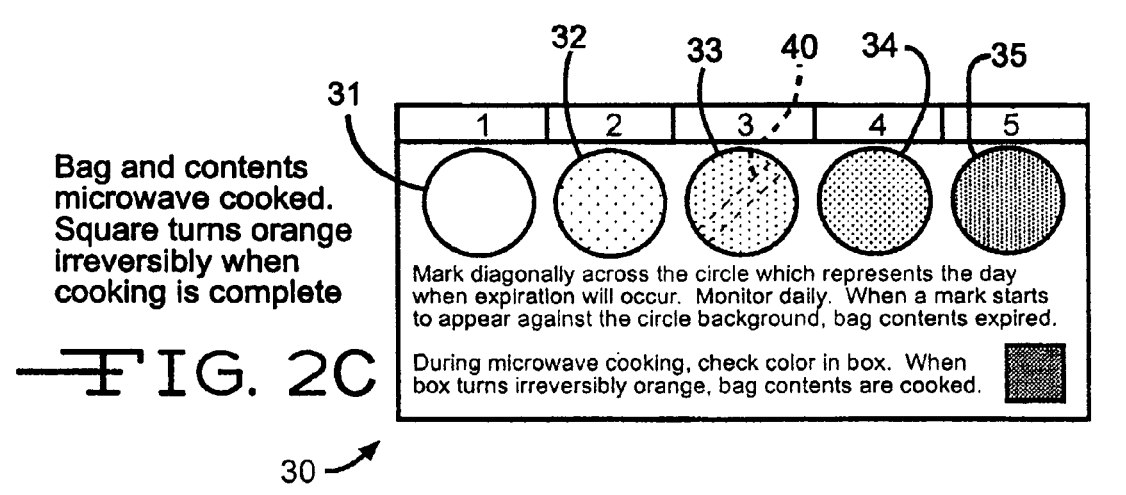

The foregoing embodiment is illustrated in FIGS. 2A, 2B and 2C, where there is shown a label 30 prepared to monitor and indicate both food product expiration and cooking. Similar to the embodiment of FIGS. 1A, 1B and 1C, the label 30 had printed thereon five circles 31, 32, 33, 34 and 35 representing the days. The circles 32, 33, 34 and 35 had printed therein blue ranging from a light blue tint in circle 32 and increasingly greater tint in circle 33, more in circle 34 to the greatest amount of tint in circle 35. As in the previous embodiment, no coloration was provided in the left circle, namely, circle 31. In the lower right corner of the label is a square 36 containing a prepolymerized zone with polydiacetylenic polymer of N-ethyanol-hexadeca-5,7-diyneamide (prepared synthetically). The preprinted square 36 turned blue when cold, magenta at groom temperature and irreversibly orange when elevated above 160° F.

Circle 33 was marked with a diagonal line 40 using the felt tip pen and the plural intrinsic initiation expiration indicator monomer as in the embodiment of FIGS., 1A, 1B and 1C. The goods which were expected to expire three days after purchase were removed from the refrigerator after two days and then cooked. Accordingly, the diagonal mark 40 which was marked in the circle 33 representing a day three expected expiration never became visible. Accordingly, the diagonal line 40 is shown in dashed lines.

The label 30 was applied to a combination storage, and microwave cooking bag. The bag was made with a polyester/polypropylene laminate and was heat sealed containing a meat marinade. The label 30 was marked as shown by diagonal line 40 in circle 33 for expiration on day 3 with a felt tip pen applicator containing plural intrinsic expiration indicator. The bag, containing an uncooked red meat marinade, was stored in a refrigerator and monitored twice per day each day after the label was marked. At day 2, the bag was removed and checked for perishability. No diagonal mark had yet appeared on the day 3 circle 33 indicating that the bag contents had not expired.

The bag and its contents were placed in a dish and cooked in a conventional microwave for 5 minutes. The pre-printed square 36 used for indicating cooking turned reversible from a magenta to an orange color after only 2 minutes of cooking. Since the color change indicated reversibility from an orange color back to a magenta color, the indicator signaled that cooking was not complete. The bag and contents' were cooked 3 more minutes in the microwave oven and the indicator in square 36 subsequently turned irreversibly orange indicating that cooking was complete. The internal temperature of the red meat contents was immediately measured to confirm that an internal temperature of the meat had achieved a temperature level of 160° F.

Plural indicators monitoring initial perishability, cooking completion, and post-cooking perishability: With reference to FIGS. 3A, 3B, 3C and 3D, printed labels 50 were prepared and designed similar to those described above. Instructional material and designs were developed to accommodate multiple usages including food perishability monitoring, cooking completion monitoring, and post cooking perishability monitoring.

Graphics, were printed on the label 50 such that the plural intrinsic indicating material could be marked in a predetermined rectangle. The rectangle to be marked, rectangle 51, was bordered by three colored reference rectangles 52, 53, 54. The left hand rectangle 52 was printed with a medium blue tint representing what the indicator color will be when the plural intrinsic expiration indicating material changes color to indicate that a perishable item must be cooked immediately. The upper rectangle 53 was pre-printed with a light orange tint representing what the indicator color will be when the plural intrinsic expiration indicating material changes to when the item is microwave cooked to completion. The right rectangle 54 was pre-printed to a purple hue representing what the indicator will be when the item is placed back into the refrigerator, cooled to 35-40° F. and stored for several more days.

The label 50 was applied to a combination storage and microwave cooking bag. The bag was made with a polyester/polypropylene laminate and was heat sealed containing a meat marinade. The label colors were calibrated such that it could be marked for expiration on day 3 of storage as previously described with a felt tip pen applicator (see example above: "Plural intrinsic expiration indicator felt tip ink pen applicator"). The bag, containing an uncooked red meat marinade, was stored in a refrigerator and monitored twice per day each day after the label was marked. At day 2, the bag was removed and checked for perishability. The mark in rectangle 51 had not yet turned to the reference color blue after two days of refrigeration. On the day 3 of refrigeration, the mark became the same blue hue as the reference color in rectangle 52 (see FIG. 3B) indicating that the bag contents should be used immediately.

Figure 3A:
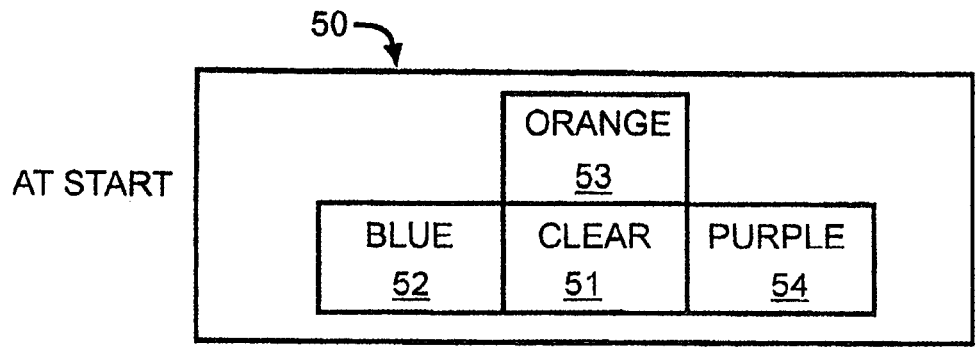
FIG. 3A shows an alternative label of the present invention designed to monitor and designate initial perishability, cooking, completion, and post cooking perishability.
Figure 3B:
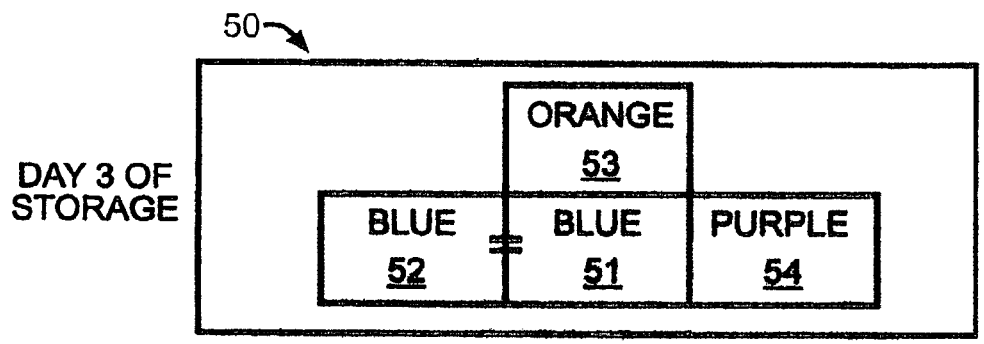
FIG. 3B shows the label of FIG. 3A at day three of storage.
Figure 3C:
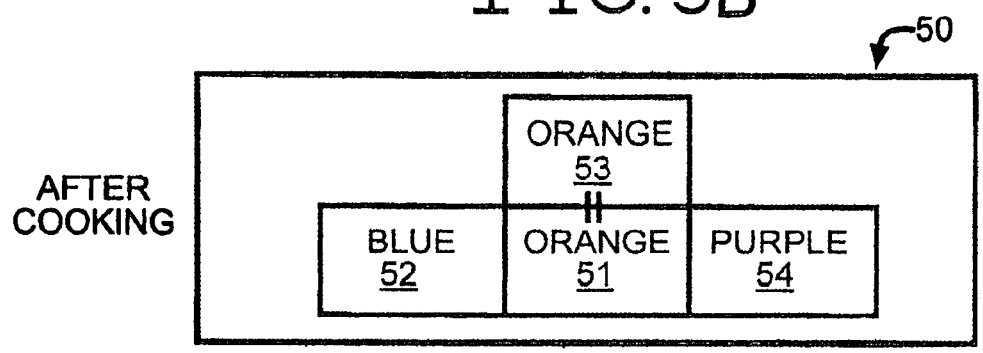
FIG. 3C shows the label of FIG. 3A after three days of storage and then complete cooking.
Figure 3D:
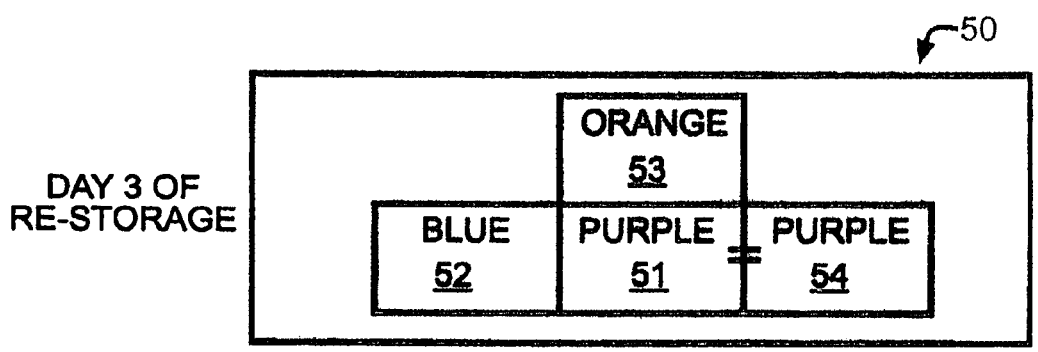
FIG. 3D shows the label of FIG. 2A after three days of storage, complete cooking, and three days of post cooking storage.

The bag and its contents were placed in a dish and cooked in a conventional microwave for 5 minutes. The marked rectangle 51 turned reversible from a magenta to a orange color after only 2 minutes of cooking. (See FIG. 3C). Since the color change indicated reversibility from an orange color back to a magenta color, the indicator signaled that cooking was not complete. The bag and contents were, cooked 3 more minutes in the microwave oven and the marked square subsequently turned irreversibly orange indicating that cooking was complete when compared to the reference orange rectangle as shown in FIG. 3C. The internal temperature of the red meat contents was immediately measured to confirm an internal temperature of the meat had achieved a temperature level of 160° F.

Immediately after cooking, the bag was placed in a refrigerator (35-40° F.). The marked center rectangle 51 was initially orange on the first day. (See FIG. 3C). The marked rectangle gradually turned from an orange color to a purple color after continued refrigeration for 3 subsequent days. (See FIG. 3D). On the third complete day of refrigeration, the mark rectangle 51 had the same coloration and hue as the right hand rectangle 54 indicating that bag contents, post cooking and refrigeration should be consumed immediately or disposed.

Semi-automated label dispenser with internal marker for plural intrinsic expiration indication: A semi-automated label dispenser for issuing pre-marked plural intrinsic expiration indicating labels was constructed. Labels with pre-printed graphics were prepare using flexographic printing using a geometry and graphics described earlier. Rolls containing 250 die-cut labels were placed in a dispenser apparatus containing a digital counter, motorized dispenser, ink fluid reservoir, felt-tip pen applicator, a digital processing algorithm, a digital display, and a numeric key board.

The labels and semi-automated dispenser were registered such that when a day for expiration was typed in on the key pad, the dispenser would appropriately mark and dispense a label. The printing mechanism also incorporated the ability to print times and dates for activation on the label. Dispensed labels could be directly placed on a storage container containing a perishable product of interest. Labels were utilized as described above and monitored for expiration of the food contents they were used with.

Pre-portioned bags imprinted with graphics and substrate compatible with the plural intrinsic expiration initiation indicator: Flexographic fluid inks (Fluid Ink Technology, Inc.) were used to print regions on plastic bags (treated or untreated polypropylene and polyethylene). A white background ink was printed and dried on polyethylene bags. A 3 inch by 4 inch rectangular region was printed using a standard transfer printing process. A printed graphic similar to that described above in the example "Printed DISSOLVE-A-WAY® labels for plural time/temperature and temperature monitoring devices" was printed in the center of a 6 inch by 8 inch bag. The bag was used identically as that described in the example "Printed DISSOLVE-A-WAY® labels for plural time/temperature and temperature monitoring devices" (FIGS. 1A, 1B and 1C). The printed region of the bag remained permanently attached to the bag.

Home-use water portable filter indicator for reporting time for filter chance: A label-based indicator was produced with a removable adhesive backing for placement on a home use water filtration unit (Brita Water Filtration Systems, Brita Products Company). The label had graphics printed to communicate and instruct the user when it was time to change the water filter in the unit. The graphic had blue printed horizontal bar as a reference color and open bar with a white background running parallel and adjacent to the blue printed horizontal bar. The open bar with white background was intended to be the area to be marked with the intrinsic expiration indicator.

Instructions were printed on the label indicating that when a pen filled with the intrinsic expiration indicating material was used to mark the open bar. A color would appear at the end of a 2 month period which was equal in hue and intensity as the blue printed horizontal bar. When a filter was changed in the unit, the user marked the open bar area with a pen containing a intrinsic expiration indicating material formulation. For the purpose of prolonged expiration (2 months at room temperature), a formulation was used containing a mixture of 150 mg/ml 10,12-tricosadiynoic acid (GFS Chemical, Inc.) and 15 mg/ml 10,12-pentacosadiynoic acid (GFS Chemical, Inc.) in a solvent system consisting of ethanol/chloroform (Aldrich Chemical, Inc.) 2/1 volume/volume. This mixture and concentration of diacetylenic monomers was selected based on its coloration over prolonged periods of time at room temperature. The mixture was added to an empty felt tip pen for application to the descriptive label.

Pre-colored/polymerized plural intrinsic expiration indicator zone for mark through inactive plural intrinsic expiration indicator: Pre-colored/polymerized plural intrinsic expiration indicating materials were made by pre-coating and pre-polymerizing the material in a selected zone on a label. An ink solution described above in the example "Solvent based ink formulation" was printed on a substrate to serve as the reference background for marking with a solvent soluble monomeric intrinsic indicator. The zone was pre-polymerized with a hand held ultraviolet lamp (254 nanometer) and calibrated in coloration intensity to a hue which represented the coloration that the plural intrinsic expiration indicating material would naturally turn to in a refrigerator after 3 days of storage (UV exposure for approximately 3 seconds at 12 inches). The zone was printed on a label with graphics and instructions for use.

For use, the label was attached to a pre-portion bag filled with raw red meat for storage. The color intensity of the pre-polymerized zone was adjusted in intensity such that, when marked with a strike through mark of the plural intrinsic expiration indicating material using a felt tip pen, the marked area would turn color to match the background color of the pre-polymerized zone background. The mark was made with a felt tip pen described above in the example "Monomer felt tip ink pen applicator". Upon marking, the marked area caused the underlying pre-polymerized zone to turn orange due to the solvent triggering from the felt tip pen ink solvent.

The label was applied to a storage bag. The bag was made with a polyester/polypropylene laminate and was heat sealed containing a meat marinade. The label was marked for expiration on day 3 as previously described. The bag, containing an uncooked red meat marinade, was stored in a refrigerator and monitored twice per day each day after the label was marked. At day 2, the bag was removed and checked for perishability. The mark remained orange/purple and had not yet turned blue. Perishability was calibrated to be judged to occur when the orange mark turned the same blue color as the background pre-polymerized zone. At day 3 from marking and initial storage, the mark appeared to have the same background color as the pre-polymerized zone and, therefore, indicated that the perishable meat contents should be used that day or disposed.

Further, the mark was calibrated along with the pre-polymerized background color that if the mark turned a darker blue than the pre-polymerized background color, then the contents of the bag had expired and should be disposed of rather than cooked and eaten.

This format has the advantage that the solvent in the application device can immediately trigger a color change in the pre-colored/polymerized background indicating that the application device is charged with the solvent solution and is not dried out. In addition, the solvent/monomer solution delivered to the substrate surface could be easily located on the background by triggered mark. As the time/temperature process ensues, the expiration indication can be visualized by a color change in the mark. The mark will change color over time and depending on temperature to become the same color as the background pre-colored/polymer. The background color could be calibrated and used as a reference color for indicating what the final color of the indicator should be in order to indicate when an attached item is perished.

Plural device with solvent saturated inactivation strip enclosure activated by removing seal: An alternative activation means was created by saturating a paper strip with the monomer ink formulation described above (see example: "Solvent based ink formulation") and then sealing the paper strip in a polyester plastic barrier. The monomer remained inactive in the solvated state and until the plastic barrier was removed. Removal of the barrier permitted the solvent to evaporate thereby depositing dried plural intrinsic expiration initiation material on the paper surface. The deposition of solid material initiated the process of coloration.

A strip of standard white filter paper (Whatman no. 2) was cut to a 0.5 inch by 1 inch in dimension. The paper strip was placed and centered on a heat sealable polyester strip 0.75 inch by 2 inch in dimension. The strip was saturated with several drops of monomer ink formulation (above). A second heat sealable polyester strip with the same dimensions as the first polyester strip was placed over the paper strip and laminated to the lower polyester strip using mild heat sealing. The solvent saturated paper was hermetically sealed during the process. The monomer ink formulation remained saturated after the sealing process.

A light blue reference decal (0.24 inch in diameter) was adhered to the end of one side of the outer part of the polyester enclosure such that none of the paper strip was obscured. The reference decal was calibrated in hue as to what the final color of the plural intrinsic expiration initiation material coloration would be after 3 days exposure in a refrigerator.

The polyester enclosure was designed in a way that permitted the easy peeling of the upper strip from the lower strip while maintaining the presence of the blue tinted reference color decal. The strip could be activated by peeling off the upper polyester strip while keeping the rest of the device intact.

The strip was adhered to a plastic bag containing a red meat and marinade. The bag, contents and indicating strip were placed in a refrigerator (35-40° F.). After adherence using double stick tape, the strip was activated by peeling off the upper polyester strip. The solvent evaporated and the time/temperature monitoring process was initiated. The strip coloration was monitored over several days. The strip turned to an identical light blue color after 3 days in the refrigerator indicating that the meat should be cooked on that day since it was the same color as the blue tinted reference decal.

It was further determined that the strip could be used to monitor cooking progression as described above (see example: Plurality device for time/temperature and 160° F. irreversible color change indicating subsequent cooking completion). The blue coloration of the strip could be used to monitor cooking completion in a microwave oven since the plural, intrinsic expiration indicator turned an orange color irreversibly above 160° F.

Plural intrinsic expiration initiation device on pre-printed porous substrate to control coloration degree: DISSOLVE-A-WAY® labels, were printed similar to the example above ("Printed DISSOLVE-A-WAY® labels for plural time/temperature and temperature monitoring devices"). Solvent impermeable flexographic inks were used in the printing process. The color and hue were matched to a light blue (pantone color match). A screen pattern of dots (0.01 millimeter dia.) were printed from a percent coverage of 2%, 4%, 8%, 16%, 32% and 74% total area from the lowest percent on the left to the highest percent on the right. The dot patterns were printed in circles 1.0 cm in diameter with a dark blue 1 millimeter diameter ring as a border around each circle. The circles were printed side-by-side 1.3 cm center-to-center. An additional clear circle was printed to the left of the printed circles such that there were a total of 7 circles lined up side-by-side. The circles were marked above to indicate day 1 through day 7 of expiration.

The labels were used in an application similar to that described above ("Printed DISSOLVE-A-WAY® labels for plural time/temperature and temperature monitoring devices"). The circle representing day 3 of expiration was marked with the monomer felt tip ink pen applicator containing the plural intrinsic initiation expiration indicating material described above ("Plural intrinsic expiration indicator felt tip pen applicator").

As is evident by the description above and various examples, the subject invention provides for numerous advantages. The plurality of color changes provide for a continuum of perishable handling and processing means which can be simultaneously or sequentially monitored. The monitoring process is simplified by the visual appearance of discrete color changes that the indicating material undergoes during color changing traditions. Devices are activated at the point of usage rather than requiring cold storage or other inconvenient storage means to inhibit the initiation process. Devices can be made with simple low cost substrate and the plural intrinsic material can be deposited on to a substrate using a convenient low cost application means such as marking with a felt tip pen.

Various geometries and configurations can be incorporated since the substrates can be made using conventional papers, labels and printing processes. Thus, processes for production can utilize existing high speed printing process for mass production at low costs. Monomeric diacetylenic compounds can be readily adjusted in structure to accommodate particular applications. Temperature and time frame for color development and plurality application can be assessed to design and synthesize a particular diacetylenic monomer with the attributes for a given application. Diacetylenic chemistries provide for the indicating material to be made reversible or irreversible depending on the application. Finally, the devices and indicators have broad application across various perishable and time indicating applications.

Plural Polymeric Time-Temperature Substrates

The plural intrinsic time-temperature indicating system can be utilized such that the time-temperature indicating material is pre-polymerized in one colored state and caused to change color to a second state by an activating agent that interacts with the polymer polydiacetylene to induce the color change. A solublized form of the diacetylenic monomer can be coated on to the surface of a substrate and polymerized to a polydiacetylene polymer. The polydiacetylene polymer can respond to an activating agent by contacting the activating agent to the surface of a polydiacetylene layer. The activating agent can cause the polydiacetylene layer to change color from a deep blue color to a bright red hue. The degree and rate of color change is time temperature dependent. Time-temperature indicators are conveniently prepared by utilizing coated substrates with a polymerized polydiacetylenic layer and subsequently contacting the layer with an appropriate activating or triggering agent that cause the layer to change from one color to another. Low reaction temperatures (30-60° F.) are prolonged and high reaction temperatures (60-90° F.) are accelerated. Plural time-temperature/temperature or other formats are made possible by utilizing adjacent areas of the polydiacetylene-coated substrate as a temperature indicator or to other indication means.

Formats

A variety of formats can be used for revealing relevant messages to users of the plural intrinsic time-temperature indicating system. Messages can be under or over-printed using a stationary ink that is obscured by the time-temperature indicating ink. The message can be revealed upon time-temperature indication and a color change in the time-temperature material relative to the stationary ink. Messages can be printed in the exact hue and color of the time-temperature ink and surrounded by the time-temperature ink such that the color and contrast of each ink type gives the visual appearance of no message until the message is revealed. Messages can be selectively generated on a printed time-temperature substrate by first creating a patterned or printed message in a time-temperature activating material that comes in contact with the initially colorized time-temperature substrate. When the printed or patterned activating element is contacted with the time-temperature indicating material, only the printed message will be highlighted to change color and give the appearance of revealing a message.

Time-temperature triggering can be accomplished by introducing an active triggering agent into the substrate in a dried form. The active triggering agent is released from the substrate and allowed to interact with the polydiacetylene layer in a time-temperature format when a solublizing agent is applied to the substrate. Upon application of the solublizing agent, the active triggering agent is mobilized.

The substrate can have a printed immobilized triggering agent on its surface or embedded and contiguous with the substrate surface. The agent would be selected such that it would not have any initial color. The agent could be printed in a useful message form. The time-temperature material can be subsequently over printed over the latent printed triggering agent. The triggering agent in its latent form is able to initiate a color change in the time-temperature material since it is not mobile and can not diffuse without the addition of a diffusion stimulating or solublizing agent. The time-temperature process can be initiated by applying a solublizing agent to the substrate surface directly over the time-temperature material and over the region where the triggering agent has been printed and immobilized. When the solublizing agent has saturated the substrate surface, the triggering agent is mobilized, made free to diffuse and can interact with the time-temperature material so as to initiate a color change in the time-temperature material. Both diffusion and stimulation of a color change in the time-temperature material are both diffusion dependent and can be made to work cooperatively to prolong or reduce the time-temperature effect.

Solublizing agents can include water, polyethylene glycol, glycerol, inert oils that themselves do not cause a triggering effect in polydiacetylene, inert silicon oils, inert non-volatile solvents (e.g. dimethylformamide), hydrating gels, and the like. The solublizing agents will typically be present at 100% concentrations, but can be present in mixtures and at concentrations that are required for a particular application.

Various bar code elements or lines can be made to be more or less time-temperature responsive. One or more bar code lines or portions of lines can be printed with the time-temperature material such that an initial scan, prior to a time-temperature event, can be used as a calibration event. As the time-temperature process is triggered with an activating agent, certain elements of a bar code begin to change. A subsequent scan can be used to monitor the progression of the time-temperature process and quantitatively report the status of the food type being monitored. The bar code can also possess a temperature only dependent element that will change color when a specific temperature such as a cooking temperature is achieved, therefore, providing for a time-temperature/temperature plural intrinsic indicator.

Laminated contact configurations can be utilized for accurate delivery and metering of the activating agent placed in contact with the time-temperature coated substrate. Laminated contact configurations involve coating an activating agent on one substrate element and coating the time-temperature indicating polydiacetylene polymer on a second substrate. Initiation of the time-temperature process requires that the two substrates are laminated together such that the activating agent is placed in direct proximal contact with the polydiacetylene layer. The contact between layers can be maintained during the time-temperature indicating process.

Various laminating contact configurations are possible. The time-temperature polydiacetylene layer can be adhered to a transparent flexible substrate and be applied to an affixed opaque substrate containing the activating agent. Alternatively, the activating agent can be adhered to a transparent flexible substrate and applied to an affixed opaque substrate containing the time-temperature sensitive polydiacetylene layer. Each configuration ban lead to the same result; however, production and packaging of the product formats will vary depending on the product configuration of choice.

Laminating substrates used for delivering either the time-temperature indicating polydiacetylene or the time-temperature activating agent can be made flexible or rigid. The substrate can be patterned with the material to be delivered or can be simple and non-patterned. The material can be flood coated or applied in a % dot pattern. The material can be printed into a message form for revealing a message or deliver a simple mark circle, or icon. The material can be in a viscous gel from or in a more permanent adhesive form such as the adhesive on a tape. Adhesives on a tape can be impregnated or formulated with the material of interest such that the laminating process involves simply attaching a tape piece to the apposing substrate for initiating the process.

The laminating substrate can be made of any of a variety of materials including transparent plastic, tape, thin almost transparent Dissolve-A-Way® label stock, water soluble materials such as those used in breath strips, nitrocellulose-based materials, wax papers, cellophane, vinyl, polyvinyl acetate, polypropylene, polyethylene, acrylic, polystyrene, any of a variety of suitable plastic compositions, glass, foils, films, acetate transparency materials, adhesive substrates, elastic compositions, food grade materials or the like.

Substrates

A wide range of substrate types can find use for producing plural intrinsic time-temperature indicators. Paper, plastic, plastic sheet, Tyvek™ sheet, fiber, glass, metal, composite materials, fibrous materials, compounded materials, coated materials, painted surfaces, Dissolve-A-Way® materials, printed surfaces and the like can be used. The substrate can be a pressure sensitive label, be adhesive or non-adhesive, can be thick or thin, can be flexible or rigid, can be laminated or unlaminated, can be clear or opaque, can be smooth or rough, or can be coated or uncoated. Coated substrate areas can be continuous or discontinuous. Discontinuous substrate coatings or variable substrate coatings can find use as a means to regulate the sensitivity of a time-temperature indicator. The substrate surface should be compatible with food or substances intended to be monitored. The substrate can be a part of a container of food, attached to a container of food, or used along with a container of food.

Substrates can come in various thicknesses depending on the intended application of interest. Substrates can range from 0.1/1000 to 250/1000 of an inch thick. More often, substrates will range from 1/000 to 100/1000 of an inch thick. Usually, selected substrates will range from 2/1000 to 20/1000 of an inch thick. The thickness will more often depend on the product format rather than the functionality of the time-temperature indicating process. The substrate flexibility will be important particularly when it will be applied to a surface intended to be monitored for the purpose of monitoring a time temperature process.

Indicating Compositions

Monomer type diacetylenic monomers can be selected based on their reactivity for a particular use as a time-temperature indicator or plural intrinsic indicator. Medium to long chain diactylenic fatty acids find use to comprise time-temperature indicators. The diacetylenic compound can be shorter in length for increased reactivity (14 carbon atoms in length) or longer in length for reduced activity (25 atoms in length or more). Typically carboxylated head groups such as a carboxylic acid can be utilized to facilitate an irreversible and permanent color change during a time-temperature indication process. Representative compounds include 10,12-tricosadiynoic acid (23 carbon atoms in length) and 10,12-pentacosadiynoic acid (25 carbon atoms in length).

The diacetylenic group can be positioned closer or more distil to the lipid's polar head group. The diacetylene moiety can be 2 to 18 carbons away from the polar head group in the 2, 4; 3, 5; 4, 6; 5, 7; 6, 8; 7, 9; 8, 10; 9, 11; 10, 12; 13, 15; 14, 16; 15, 17; or 18, 20 positions. More often the diacetylene moiety will be in the 3, 5 to 14, 16 position and most often, the diacetylene moiety will be in the 5, 7 to 10, 12 position. The exact position will depend on the application of interest and synthesis procedures required for making the compound of interest.

Coating compositions comprising the diacetylenic monomer are conveniently prepared by dissolving the monomeric diacetylene material in an organic solvent or solvent-based ink. Typical organic solvents including ethanol, propanol, acetone, chloroform, dichloromethane, ethyl acetate, diacetone solvents, diethyl ether, hexane, benzene, and the like can be used accordingly to dissolve the diacetylenic monomer. Concentrations for coating compositions can range from 500 mg/ml to 1.0 mg/ml. More usually, concentrations will range from 250 mg/ml to 10 mg/ml. Typically, concentrations will range from 150 mg/ml to 50 mg/ml.

The coating composition can be comprised purely of an evaporating solvent and the diacetylenic monomer or can include a resin or matrix that becomes co-dried along with the monomer. The resin or matrix can include materials that act as binders to enhance the binding of the diacetylenic material to the substrate. Resins or matrix components can include nitrocellulose, adhesives, plastics, gums, waxes, pigments, or the like which do not interfere with the diacetylenic material's ability to polymerize and act as a time-temperature indicator.

The coating composition can be ink jet printed, sprayed, painted, layered, dip coated, nebulized, dropped, applied with an applicator, applied with a pen or felt tip, applied by blotting, printed flexographically, printed by off-set printing, printed digitally, printed using methods such as Indigo™ printing, Gravier printing, and the like. The printing process utilized must be capable of delivering a uniform coating of the diacetylene monomer such that the monomer can be evenly distributed into a microcrystalline layer on the surface of the substrate.

Substrates comprising an evenly distributed microcrystalline layer of diacetylenic monomeric material can be exposed to ultraviolet light (254 nanometers). The monomeric diacetylenic crystals turn from a colorless to blue color upon exposure to ultraviolet light. The blue color intensity can be adjusted from very light blue colors to deep dark blue/black hues. A time-temperature polydiacetylene coated substrate can be adjusted to be more or less to a time-temperature sensitive to activating agents depending on the level of ultraviolet light exposure and subsequent level of polymerization. Low levels of polymerization resulting in light blue polydiacetylene coatings typically results in more sensitive time-temperature substrates. High levels of polymerization resulting in dark blue polydiacetylene coatings typically results in less sensitive time-temperature coatings.

Activating/Triggering Agents

Activating agents capable of inducing a time-temperature color change transition in polydiacetylene include aggressive solvents, oils, balms, acids, bases, flavors and aromas in an oil/liquid form, lubricants, menthol based compositions, polymer based oils, essential oils and a variety harsh organic or inorganic compositions that can disrupt the oriented blue form of polydiacetylenic crystals thereby inducing a color change from the blue form of the polymer to a red form of the polymer.

Activators include various cooking oils, balms, natural oils such clove, peppermint, and spearmint, greases, butter, saturated and unsaturated fats, and a variety of other fat or solvent based materials which when in contact with the blue form of a polydiacetylenic material converted the polydiacetylene to the red form. Activators were further selected based on their ability to trigger the temperature transition rapidly at room temperature from 1 to 4 hours and slowly at chilled temperatures from 2 to 4 days.

It is important that the activating/triggering agent remains localized, adhered to, and concentrated on a printed polydiacetylenic substrate during the duration of a time-temperature indicating period. Placement, uniformity of application, physical state, and adequate agent diffusion all play a role in maintaining the adequacy of the triggering effect during the indication process.

Activating/triggering agents can be used in a pure form or added in concentrations to an inert carrier composition that itself does not impart any triggering characteristics. The activating agent can be present from 0.001% to 100%. Usually, the activating agent will be present from 0.01% to 90% in an inert carrier matrix. More usually, the activating agent will be present from 0.1% to 50% in an inert carrier matrix. Typically, the activating agent will be utilized from 0.1% to 10% in an inert carrier matrix.

The inert carrier matrix is selected based on its characteristics for mobilizing and transporting the activating/triggering agent to interact with the time-temperature indicating polydiacetylene material coated on a substrate. It is desirable that the activating/triggering agent is solublized and evenly distributed in the matrix of the inert carrier composition. Likewise, it is desirable that the inert carrier matrix has the property of low volatility to ensure that it does not evaporate during the time-temperature indicating process. The inert carrier matrix should facilitate good diffusion of the activating/triggering agent. The inert carrier matrix should remain in a fluid form without crystallizing during low-temperature time-temperature indication. The inert carrier matrix should maintain good solublization of the activating/triggering agent through out various temperature ranges that the time-temperature system is to be utilized.

The inert carrier matrix can be formulated with inactive oils, polyethylene glycols, polypropylene glycols, glycerol, low viscosity polyvinyl acetates, adhesive compositions, Interlemer™ compositions, low melting waxes, inert silicon oils, inert hydrocarbon oils, low viscosity and diffusing materials such as silicon rubbers, gels, gelatins, gums and the like. The inert carrier matrix selected will, depending on the physical, chemical, and commercial considerations, be involved in the final product.

Figure 4A:
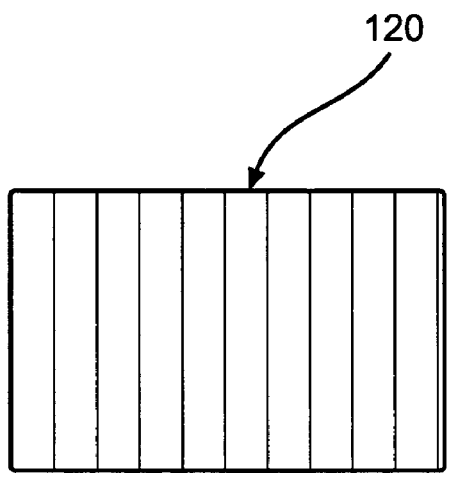
FIGS. 4A, 4B, 4C and 4D show a label prepared in accordance with the present invention and showing color changes of various portions thereof in response to time-temperature and temperature factors.
Figure 4B:
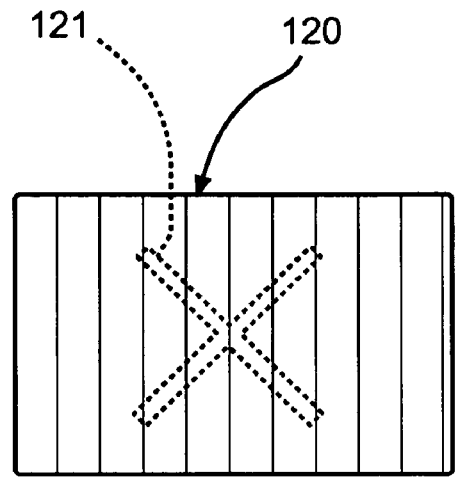
Figure 4C:
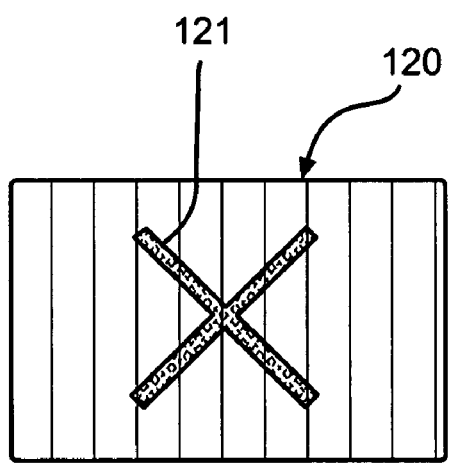
Figure 4D:
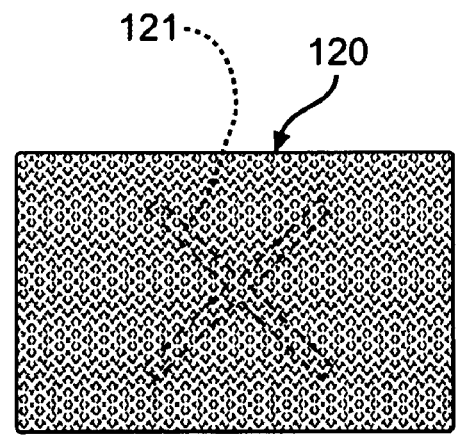

Referring to FIGS. 4A, 4B, 4C and 4D, there is shown a time-temperature and temperature monitoring marking device in the form of label 120. The label 120 has printed thereon a diacetylenic monomer which was polymerized to a polydiacetylene polymer as discussed in Example 1 below. Thereafter, a transparent activating agent, for example, a mint lip balm such as one manufactured by Blistex Corporation, was applied in the shape of an X as designed by the numeral 121. As shown in FIG. 4B, the mark X 121 is shown in dashed lines as it was transparent and not readily visible. The balm serves as the time-temperature activating agent. After a specified length of time at a specified temperature, the X mark 121 causes the activated polydiacetylene polymer underlying the mark X 121 to turn from a dark blue color to a bright red/orange in a two to four day time period at 45° F. or in two to four hours at room temperature. The remaining surface portion of the label 120'outside of the X-mark 121' area remains the dark blue color as shown in FIG. 4C. At such time as the label is brought to a high threshold temperature, for example 140° F., the portion of the label outside of the X-mark 121 will change to a bright orange as shown in FIG. 4D.

Examples 1, 2 and 3 provide further details of the specific labels and tests related to the embodiment of FIGS. 4A, 4B, 4C and 4D.

EXAMPLES

Example 1

Preparing ink jet printed time-temperature/temperature pressure sensitive Dissolve-A-Way® label substrates: Dissolve-A-Way® label (DayMark Corporation) was ink jet printed using a solution of 150 mg/ml 10,12-tricosadiynoic acid dissolved in chloroform/ethanol 1/1 v/v. Dissolve-A-Way® sheets were cut to 8.5 inch by 11 inch and inserted into an ink jet printer (HP PSC 2210). The print setting was configured for photo-quality to ensure the highest ink delivery. The black ink jet cartridge was utilized for delivering the time-temperature ink composition. An empty cartridge was opened by removing the top plate, thoroughly cleaned with water and then rinsed and dried with ethanol. The cartridge was filled with 10 ml aliquots of solution (above), re-inserted in the printer and printing initiated. Solid print areas were designated that completely covered the page with the exception of a slim border. Printed sheets were activated by polymerization with ultraviolet light (254 nm). A 6 bulb (18 inch low pressure mercury vapor) light bank was used for polymerization. The distance between the sheet and printed substrate was maintained at 18 inches. The degree of polymerization was established by controlling the total exposure time. Upon polymerization, the white printed sheets turned intensely blue.

A mint lip balm (Blistex Corporation) was used as the time-temperature activating agent. Balm marks were applied in generous marks at room temperature. Half of the marked Dissolve-A-Way® pieces were left at room temperature and the other half were placed in a refrigerator at 45° F.

The marked Dissolve-A-Way® pieces kept at room temperature transitioned from a deep blue color to a bright orange color within a 4 hour period. Each of 4 marks were consistent in the time and degree of color change. The marked pieces kept at 45° F. transitioned from a deep blue color to an orange color by the end of 4 days. Each of 4 marks exhibited consistency in color change over the time period.

The blue printed areas surrounding the marked areas on the chilled substrates remained temperature active. The surrounding areas that remained blue exhibited a strong plural intrinsic thermochromic effect. As a piece of the printed Dissolve-A-Way® substrate was attached to a microwavable piece of meat sealed in a plastic tub and heated, the surrounding blue area transitioned to a bright orange to match the color change of the area that had been triggered to change color during the time-temperature indication period. The temperature dependent color change of the surrounding blue area occurred irreversibly at 160° F. Subsequently, the Dissolve-A-Way® time-temperature pieces were easily and readily removed from the plastic tub by contact with water. The label and its composition immediately dissolved into the water.

Example 2

Preparing ink jet printed time-temperature/temperature Tyvek™ substrates: The plastic film Tyvek™ (Du Pont Company) was ink jet printed using a solution of 150 mg/ml 10,12-tricosadiynoic acid dissolved in chloroform/ethanol 1/1 v/v. Tyvek™ sheets were cut to 8.5 inch by 11 inch and inserted into an ink jet printer (HP PSC 2210). The print setting was configured for photo-quality to ensure the highest ink delivery. The black ink jet cartridge was utilized for delivering the time-temperature ink composition. An empty cartridge was opened by removing the top plate, thoroughly cleaned with water and then rinsed and dried with ethanol. The cartridge was filled with 10 ml aliquots of solution (above), re-inserted in the printer and printing initiated. Solid print areas were designated that completely covered the page with the exception of a slim border. Printed sheets were activated by polymerization with ultraviolet light (254 nm). A 6 bulb (18 inch low pressure mercury vapor) light bank was used for polymerization. The distance between the sheet and printed substrate was maintained at 18 inch. The degree of polymerization was established by controlling the total exposure time. Upon polymerization, the white printed sheets turned intensely blue.

A mint lip balm (Blistex Corporation) was used as the time-temperature activating agent. Balm marks were applied in a generous marks at room temperature. Half of the marked Tyvek™ pieces were left at room temperature and the other half were placed in a refrigerator at 45° F.

The marked Tyvek™ pieces kept at room temperature transitioned from a deep blue color to a bright orange color within a 4 hour period. Each of 4 marks were consistent in the time and degree of color change. The marked pieces kept at 45° F. transitioned from a deep blue color to an orange color by the end of 4 days. Each of 4 marks exhibited consistency in color change over the time period.

The blue printed areas surrounding the marked areas on the chilled substrates remained temperature active. The surrounding areas that remained blue exhibited a strong plural intrinsic thermochromic effect. As a piece of the printed Tyvek™ substrate was attached to a microwavable piece of meat sealed in a plastic bag, the surrounding blue area transitioned to a bright orange to match the color change of the area that had been triggered to change color during the time-temperature indication period. The temperature dependent color change of the surrounding blue area occurred irreversibly at 160° F.

Example 3

Pre-printed plural intrinsic time-temperature indicator flexographically printed on pressure sensitive label stock: A pre-polymerize/sensitized layer of polymeric polydiacetylene was formed using a nitrocellulose ink base and printed using a flexographic printing process. The ink base was made using a common solvent-based nitrocellulose ink base used in solvent base flexographic printing process. The solvent carrier was used to dissolve a mixture of 15% by weight 10, 12 tricosadiynoic acid and 1.5% by weight 10, 12 pentacosadiynoic acids. The ink base was purchased from Wykoff Corporation. The monomeric diacetylenic acids were added to their corresponding concentrations, mixed and dissolved in the ink base.

After formulation of the ink base, the formulated ink was printed on to a pressure sensitive label stock using a flood coating technique to ensure complete coverage on the printed substrate. The printed substrate was dried using an attached blow dryer in the printing unit. After printing and drying, the formulated ink was sensitized to the polydiacetylenic form by exposure to ultraviolet light (254 nm). The polymerization process converted the uncolored white substrate to a blue color indicating the formation of the polydiacetylenic form.

The polydiacetylenic pre-polymerized layer coated on the pressure sensitive label substrate was used in a time-temperature and temperature indication trial. Time and temperature sensitive activators were used to convert the blue form of the polydiacetylenic layer to a red form by directly contacting the polydiacetylenic layer with the activator. Activators were selected based on their ability to convert the blue polydiacetylenic material to the orange form of the polydiactylenic material. A mint lip balm (Blistex Corporation) was used as an activating agent. Balm marks were applied in generous marks at room temperature. Half of the marked substrates were left at room temperature and the other half were placed in a refrigerator at 45° F.

The marked substrates kept at room temperature transitioned from a deep blue color to a bright orange color within a 4 hour period. Each of 4 marks were consistent in the time and degree of color change. The marked substrates kept at 45° F. transitioned from a deep blue color to an orange color by the end of 4 days. Each of 4 marks exhibited consistency in color change over the time period.

The blue substrate areas surrounding the marked areas on the chilled substrates remained temperature active. The surrounding areas that remained blue exhibited a strong plural intrinsic thermochromic effect. As a piece of the pressure sensitive label substrate was attached to a microwavable piece of meat sealed in a plastic bag, the surrounding blue area transitioned to a bright orange to match the color change of the area that had been activated to change color during the time-temperature indication period. The temperature dependent color change of the surrounding blue area occurred irreversibly at 160° F.

Example 4

Preparing message revealing time-temperature/temperature indicator: Dissolve-A-Way® (DayMark Corporation) pressure sensitive substrate was pre-printed using an ink jet printing means with warning messages. The warning messages included but were not limited to: "Use Immediately", "Discard", "Expired", "X-Pired", "Do Not Consume", "Reject", and related warning messages. The messages were printed with a light blue hue such that they could be obscured later with darker blue over-print of the time-temperature material.

The Dissolve-A-Way® substrate was over printed using a solution of 150 mg/ml 10,12-tricosadiynoic acid dissolved in chloroform/ethanol 1/1 v/v. Dissolve-A-Way® sheets were cut to 8.5 inch by 11 inch and inserted into an ink jet printer (HP PSC 2210). The print setting was configured for photoquality to ensure the highest ink delivery. The black ink jet cartridge was utilized for delivering the time-temperature ink composition. An empty cartridge was opened by removing the top plate, thoroughly cleaned with water and then rinsed and dried with ethanol. The cartridge was filled with 10 ml aliquots of solution (above), re-inserted in the printer and printing initiated. Solid print areas were designated that completely covered the page with the exception of a slim border. Printed sheets were activated by polymerization with ultraviolet light (254 nm). A 6 bulb (18 inch low pressure mercury vapor) light bank was used for polymerization. The distance between the sheet and printed substrate was maintained at 18 inch. The degree of polymerization was established by controlling the total exposure time.

Upon polymerization, the white printed regions and under-printed message areas turned intensely blue. The blue coloration of the time-temperature/temperature indicating polydiacetylene layer was intense enough to obscure the under-printed message regions. Under-printed messages and over-printed time-temperature colorations and intensities could readily be adjusted to provide maximum obscurity prior to activation and maximum contrast after activation and revealing.

A mint lip balm (Blistex Corporation) was used as the time-temperature activating agent. Balm marks were applied in generous marks at room temperature directly over the message printed regions. Half of the marked Dissolve-A-Way® pieces were left at room temperature and the other half were placed in a refrigerator at 45° F.

The marked Dissolve-A-Way® pieces kept at room temperature transitioned from a deep blue color to a bright orange color within a 4 hour period and revealed the underlying message. Each of 4 marks were consistent in the time and degree of color change. The marked pieces kept at 45° F. transitioned from a deep blue color to an orange color by the end of 4 days and revealed the under-printed message. Each of 4 marks exhibited consistency in color change over the time period.

The blue printed areas surrounding the marked areas on the chilled substrates remained temperature active. The surrounding areas that remained blue exhibited a strong plural intrinsic thermochromic effect. As a piece of the printed Dissolve-A-Way® substrate was attached to a microwavable piece of meat sealed in a plastic tub, the surrounding blue area transitioned to a bright orange to match the color change of the area that had been 'triggered to' change color during the time-temperature indication period. The temperature dependent color change of the surrounding blue area occurred irreversibly at 160° F. Subsequently, the Dissolve-A-Way® time-temperature pieces were easily and readily removed from the plastic tub by contact with water. The label and its composition immediately dissolved into the water.

Figure 5A:
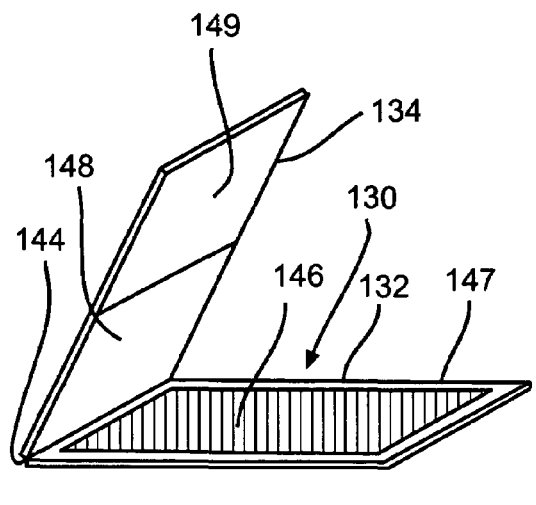
FIGS. 5A, 5B, 5C and 5D show a laminated label embodiment and showing color changes of various portions thereof in response to time-temperature and temperature factors.

Referring to FIGS. 5A, 5B, 5C and 5D, there is shown another embodiment of a time-temperature and temperature monitoring device generally designated by the numeral 130 having a plurality of layers adapted to be laminated together, namely, a first layer 132 and a second layer 134 such as a transparent tape. The first layer 132 includes a printed polymeric area 146 having a time-temperature and temperature sensitive coating such as polydiacetylene on the surface facing the second layer 134 and a border 147 around said printed polymeric area 146. The second layer 134 has one end 144 attached to one end of the first layer 132 to form a hinge. As can be seen in FIG. 5A, a first portion 148 of the laminating surface of the second layer 134 has been contacted with the activating agent such as a lip balm for example. The remaining portion 149 of the laminating surface of the second layer 134 does not have an activating agent thereon. If desired, such remaining portion 149 and/or the border 147 may have adhesive for adhering the second layer 134 to the first layer 132.

Figure 5B:
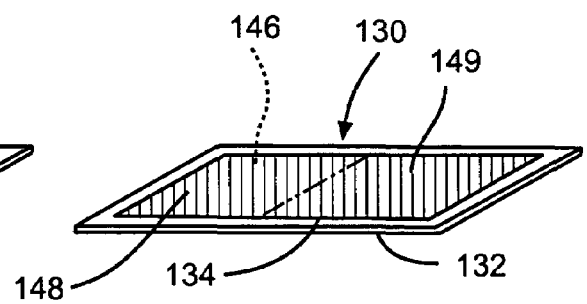

As shown in FIG. 5B, immediately after engagement of the laminating surface of the second layer 134 into interfacial relationship with the time-temperature and temperature sensitive coating of the printed polymeric area 146, said area 146 will remain its original color, blue for example, and will leave a blue appearance throughout the surface of the transparent tape functioning as the second layer 134 including that portion underlying both the first portion 148 coated with the activating agent and the second portion 149, provided the activating agent is colorless as applied.

Figure 5C:
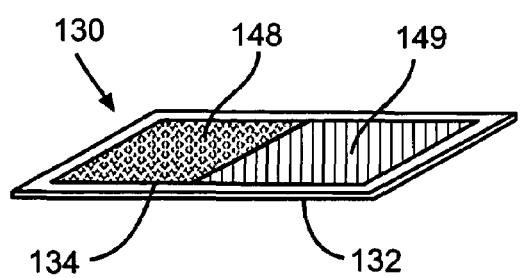
Figure 5D:
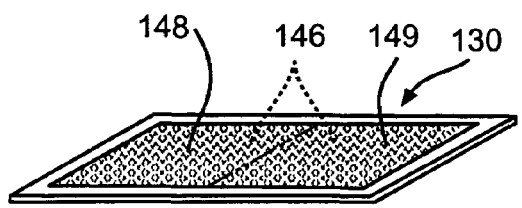

FIG. 5C shows a distinct color change in the area 143 after a period of two to four days at 45° F. or two to four hours at room temperature following engagement of the second layer 134 to the first layer 132 and activation of the polymeric coating in the printed polymeric area 146 contacted by the activating agent on the first portion 148. That portion of the area 146 not underlying the activating agent namely, the remaining portion 149 remains its original color, for example, dark blue. Thereafter, when the monitoring device 130 is heated to a specified temperature, for example 160° F., that portion of the printed polymeric area underlying the remaining portion 149 of the second layer 134 also turns to a bright red/orange matching the color of the area underlying the first portion 148 with the activating agent as shown in FIG. 5D.

Examples 5 and 6 set forth further details with respect to actual samples produced relative to the laminated embodiment of FIGS. 5A, 5B, 5C and 5D.

Example 5

Laminating time-temperature/temperature substrates: Tyvek™ (Du Pont Company) was ink jet printed using a solution of 150 mg/ml 10,12-tricosadiynoic acid dissolved in chloroform/ethanol 1/1 v/v as above. The substrate sheets were cut to 8.5 inch by 11 inch and inserted into an ink jet printer (HP PSC 2210). The print setting was configured for photo-quality to ensure the highest ink delivery. The black ink jet cartridge was utilized for delivering the time-temperature ink composition. An empty cartridge was opened by removing the top plate, thoroughly, cleaned with water and then rinsed and dried with ethanol. The cartridge was filled with 10 ml aliquots of solution (above), re-inserted in the printer and printing initiated. Solid print areas were designated that completely covered the page with the exception of a slim border. Printed sheets were activated by polymerization with ultraviolet light (254 nm). A 6 bulb (18 inch low pressure mercury vapor) light bank was used for polymerization. The distance between the sheet and printed substrate was maintained at 18 inch. The degree of polymerization was established by controlling the total exposure time. Upon polymerization the white printed sheets turned intensely blue.

A mint lip balm (Blistex Corporation) was used as the time temperature activating agent. Saturating amounts of the balm were applied to one half of a transparent tape piece (0.5 inch wide and 2 inch long). A 0.125 inch piece of tape was left uncoated at the end so as to provide for an adhesive area on both sides of the balm coated area. The tape was adhered to the time-temperature substrate such that the balm initially did not contact the substrate. Eight individual pieces with balm affixed tape strips were prepared. Half of the pieces were left at room temperature and the other half were placed in a refrigerator at 45° F. The time-temperature process was initiated by sealing the balm affixed areas to the time-temperature substrate and making complete and sealed contact with the balm to the substrate.

The pieces kept at room temperature transitioned from a deep blue color to a bright orange color within a 4 hour period. Each of 4 affixed balm areas were consistent in the time and degree of color change. The marked pieces kept at 45° F. transitioned from a deep blue color to an orange color by the end of 4 days only on the balm contact regions. Each of 4 balm affixed regions exhibited consistency in color change over the time period.

The blue printed areas surrounding the balm/tape contact areas on the chilled substrates remained temperature active. The surrounding areas that remained blue exhibited a strong plural intrinsic thermochromic effect. As a piece of the printed Tyvek™ substrate was attached to a microwavable piece of meat sealed in a plastic bag, the surrounding blue area transitioned to a bright orange to match the color change of the balm contact area that had been triggered to change color during the time-temperature indication period. The temperature dependent color change of the surrounding blue area occurred irreversibly at 160° F.

The process was repeated using a variety of different printed time-temperature substrates, time-temperature activating agents, transparent tape adhesive materials, and geometries for initiating the contact between the time-temperature system components. Both non-dissolving label material and label material of the type used for Dissolve-A-Way® labels were employed.

Example 6

Laminating dissolvable time-temperature/temperature substrates: Dissolve-A-Way® (DayMark Corporation) label was, ink jet printed using a solution of 150 mg/ml 10,12-tricosadiynoic acid dissolved in chloroform/ethanol 1/1 v/v as above. The substrate sheets were cut to 8.5 inch by 11 inch and inserted into an ink jet printer. (HP PSC 2210). The print setting was configured for photo-quality to ensure the highest ink delivery. The black ink jet cartridge was utilized for delivering the time-temperature ink composition. An empty cartridge was opened by removing the top plate, thoroughly cleaned with water and then rinsed and dried with ethanol. The cartridge was filled with 10 ml aliquots of solution (above), re-inserted in the printer and printing initiated. Solid print areas were designated that completely covered the page with the exception of a slim border. Printed sheets were activated by polymerization with ultraviolet light (254 nm). A 6 bulb (18 inch low pressure mercury vapor) light bank was used for polymerization. The distance between the sheet and printed substrate was maintained at 18 inch. The degree of polymerization was established by controlling the total exposure time. Upon polymerization, the white printed sheets turned intensely blue.

A mint lip balm (Blistex Corporation) was used as the time-temperature activating agent. Saturating amounts of the balm were applied to one half of a thin transparent piece of Dissolve-A-Way® (DayMark Corporation) label material (0.5 inch wide and 2 inch long). A section of Dissolve-A-Way® was left uncoated at the end so as to provide for an adhesive area on both sides of the balm coated area. The Dissolve-A-Way®label material was adhered to the time-temperature substrate such that the balm initially did not contact the substrate. Eight individual pieces with balm affixed were prepared. Half of the pieces were left at room temperature and the other half were placed in a refrigerator at 45° F. The time-temperature process was initiated by sealing the balm affixed areas to the time-temperature substrate and making complete and sealed contact with the balm to the substrate.

The pieces kept at room temperature transitioned from a deep blue color to a bright orange color within a 4 hour period. Each of 4 affixed balm areas were consistent in the time and degree of color change. The marked pieces kept at 45° F. transitioned from a deep blue color to an orange color by the end of 4 days only on the balm contact regions. Each of 4 balm affixed regions exhibited consistency in color change over the time period.

The blue printed areas surrounding the balm contact areas on the chilled substrates remained temperature active. The surrounding areas that remained blue exhibited a strong plural intrinsic thermochromic effect. As a piece of the printed Dissolve-A-Way® label material substrate was attached to a microwavable piece of meat sealed in a plastic bag and heated, the surrounding blue area transitioned to a bright orange to match the color change of the balm contact area that had been triggered to change color during the time-temperature indication period. The temperature dependent color change of the surrounding area from blue to orange occurred irreversibly at 160° F.

Figure 6A:
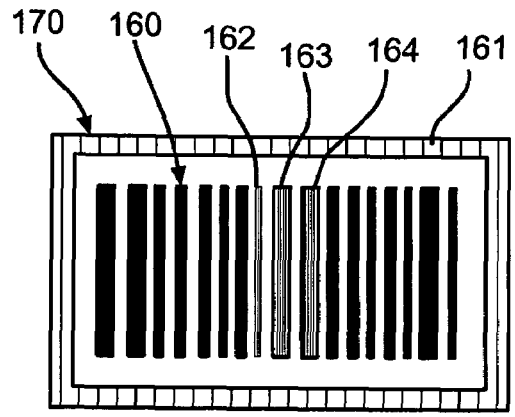
FIGS. 6A, 6B, 6C and 6D show another embodiment of label utilizing a bar code with individual bars of the code printed with various time-temperature and temperature indicators.

Referring to FIGS. 6A, 6B, 6C and 6D, there is shown a further embodiment of a time-temperature and temperature monitoring device generally designated by the numeral 170 incorporating a bar code feature 160. The device 170 includes a substrate 171 having a surface on which bars of the bar code 160 are printed. With reference to FIG. 6A, all bars of the bar code 160 except those designated by the numerals 162, 163 and 164 ate printed with a stationary fixed dark blue or black print color such as ink that is not susceptible to color change. Those bars designated by the numerals 162, 163 and 164 are printed with a time-temperature sensitive polymer, namely, polydiacetylene, which has a dark blue or black color that matches the remaining bars in the bar code 160. The bar code 160, including bars 162, 163 and 164, comprises a fully readable bar code in the initial unactivated state of bars 162, 163 and 164.

The device 170 has a border area 161 encircling the bar code 160. Polydiacetylene is also applied to the border area. As previously discussed, the polydiacetylene may initially be applied as acetylene monomer and then polymerized, for example, by subjecting it to ultraviolet light.

Figure 6B:
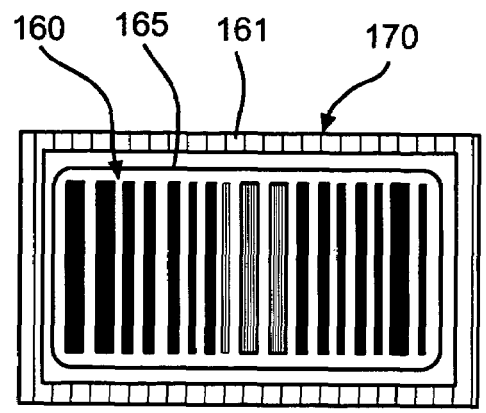

FIG. 6B shows schematically the application of an activating agent throughout zone 165 encircling the bar code 160 and, therefore applied to all bars including bars 162, 163 and 164. The activating agent is transparent and fully covers the complete bar code 160. The activating agent is not applied to the border area 161. Following initial application of the activating agent, there is no change in any of the bar members including those designated by the numerals 162, 163 and 164. However, following application of the activating agent, those bars 162, 163 and 164 printed with the time-temperature sensitive polymer will change from a dark blue/black color previously described with reference to FIG. 6A to a bright red/orange color (see FIG. 6C) after two to four days at 45° F. or two to four hours at room temperature. The change in color of the bars 162, 163 and 164 renders them unreadable by a bar code scanner with the overall result that the bar code 160 has been reconstituted to a different configuration shown in FIG. 6C thereby providing a different readable state for the bar code. The change caused by the time-temperature indication process is such that the modified bar code shown in FIG. 6C can itself act as an objective readable code to indicate food freshness for food to which the device 170 is affixed.

Figure 6C:
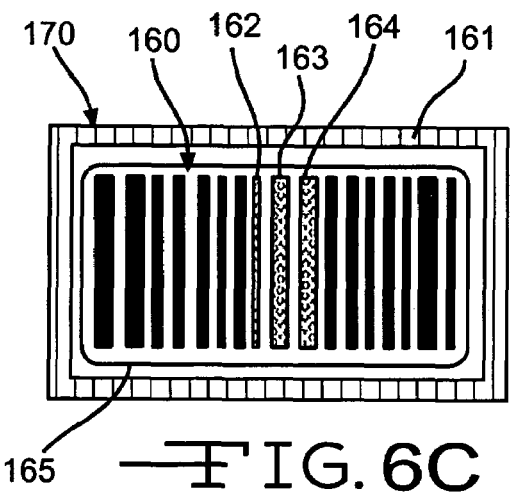
Figure 6D:
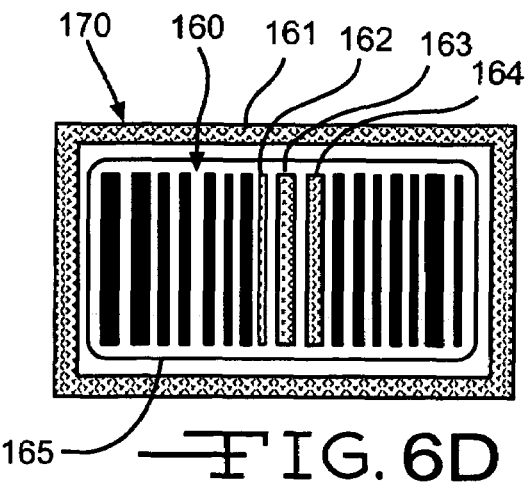

As shown in FIG. 6C, the border area 161 coated with the temperature sensitive polymer polydiacetylene remains a dark blue. Thus, the border 161 remains unaffected during the time-temperature process/transition from the condition of FIG. 6B to the condition of FIG. 6C as such border area 161 has not been contacted by the activating agent which was limited to zone 165. The border 161 remains dark blue/black at all temperatures until the device is raised to a predetermined temperature, for example 140° F. or 160° F. at which time it changes from the dark blue/black color of FIGS. 6A, 6B and 6C to a bright red/orange color as shown in FIG. 6D indicating that the food stuff to which the device is attached has been raised to the specified temperature.

Example 7

Time-temperature/temperature indicating bar code: A bar code-based system was developed such that the time-temperature and temperature change components of the plural indicating product could be read objectively with a bar code reader. Tyvek™ (Du Pont Company) was ink jet printed using a solution of 150 mg/ml 10, 12-tricosadiynoic acid dissolved in chloroform/ethanol 1/1 v/v as above. The substrate sheets' were cut to 8.5 inch by 11 inch and inserted into an ink jet printer (HP PSC 2210). The print setting was configured for photo-quality to ensure the highest ink delivery. The black ink jet cartridge was utilized for delivering the time-temperature ink composition. An empty cartridge was opened by removing the top plate, thoroughly cleaned with water and then rinsed and dried with ethanol. The cartridge was filled with 10 ml aliquots of solution (above), re-inserted in the printer and printing initiated. Bar code elements were printed using standard configurations for UPC bar codes. Printed areas were activated by polymerization with ultraviolet light (254 nm). A 6 bulb (18 inch low pressure mercury vapor) light bank was used for polymerization. The distance between the sheet and printed substrate was maintained at 18 inch. The degree of polymerization was established by controlling the total exposure time. Upon polymerization, the white printed bar code areas turned intensely blue.

UPC bar codes printed with the time-temperature material were scanned with an appropriate bar code reader. So long as the bar code retained its dark blue contrast against the white background, the bar code remained readable. When the time-temperature material transitioned from a dark blue color to a bright red/orange color, the bar code became unreadable and registered with the bar code reader as a differential result. The differential result was interpreted as a threshold time for adequate change in the time-temperature material to indicate that food held at that temperature and time should no longer be consumed.

All publications and patent applications mentioned in this specification are herein incorporated by reference to the same extent as if each individual publication or patent application was specifically indicated to be incorporated by reference.

The invention now being fully described, it will be apparent to one of ordinary skill in the art that many changes and modifications can be made thereto without departing from the spirit or scope of the appended claims.

I claim:

1. A method for monitoring plural functions of goods comprising the steps of:
   (a) providing a substrate;
   (b) applying diacetylene monomer to said substrate;
   (c) polymerizing said monomer to form a coating of polydiacetylene, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour;
   (d) providing a second layer having at least a first discrete area and a second discrete area;
   (e) applying said activating agent to said first discrete area but not to said second discrete area;
   (f) affixing said second layer to said substrate with the activating agent of said first discrete area engaging said coating;
   (g) maintaining or bringing said affixed coated substrate to a temperature below said specified temperature to cause that portion of the substrate contacted by said first discrete area to change to said second color; and
   (h) thereafter heating said coated substrate to said specified temperature to cause that portion of the substrate contacted by said second discrete area to change to said second color.

2. The method according to claim 1 further including the step of affixing said coated substrate to goods or to a container holding said goods.

3. The method according to claim 1 wherein said substrate has printed thereon a universal bar code comprising a number of discrete bars, some of said bars lying in said first discrete area and other of said bars lying inside said second discrete area.

4. The method according to claim 1, further including the step of subjecting said diacetylene monomer to ultraviolet light to thereby cause it to polymerize.

5. The method according to claim 1 wherein said activating agent is a member of the group consisting of oils, menthol, organic and inorganic acids and bases, balm compositions and organic flavors and aromatics.

6. A method for monitoring expiration of goods comprising
(a) providing a substrate having a surface with first and second discrete areas;
(b) applying a bar code to said surface, said bar code comprising a series of discrete marks, said discrete marks formed using diacetylene monomer some but not all of said discrete marks lying within said first discrete area;
(c) directing ultraviolet light to said surface to polymerize said diacetylene monomer to form polydiacetylene, said polydiacetylene having the property of (1) changing from a first color irreversibly to a second color immediately upon being subjected to a specified temperature and (2), upon activation contact by an activating agent, changing from said first color to said second color at a temperature lower than said specified temperature after a time delay of at least one hour;
(d) applying said activating agent to said discrete marks in said first discrete area but not in said second discrete area;
(e) affixing said substrate to goods or to a container containing said goods; and,
(f) heating said goods to cooking temperature above said specified temperature.

7. The method according to claim 6 wherein said activating agent is a member of the group of oils, methol, organic and inorganic acids and bases, balm compositions and organic flavors and aromatics.

8. A method for monitoring plural functions of goods comprising the steps of:
(a) providing a substrate;
(b) applying to said substrate a universal bar code comprising a number of discrete bars, some of said bars being printed with a polydiacetylene coating, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour;
(c) applying said coating to said substrate in an area spaced from said discrete bars printed with said coating;
(d) applying said activating agent to some but not all of said bars printed with said coating;
(e) affixing said substrate with said coating to said goods or to a container containing such goods;
(f) maintaining or bringing said affixed substrate to a temperature lower than said specified temperature; and
(g) thereafter heating said substrate to said specified temperature.

9. The method according to claim 8 further including the step of maintaining said affixed substrate below said specified temperature for such period of time as to cause the bars printed with said coating and contacted by said activating agent to change to said second color.

10. The method according to claim 8 wherein said activating agent is applied to said bars printed with said coating after affixing said substrate to said goods or said container.

11. The method according to claim 8 wherein said coating is applied by first applying a diacetylenic monomer and thereafter polymerizing it to a polydiacetylene polymer.

12. The method according to claim 11, further including the step of subjecting said diacetyenic monomer to ultraviolet light to thereby cause it to polymerize.

13. A device for monitoring plural functions of goods comprising:
(a) a substrate;
(b) a polydiacetylene coating on first and second discrete areas of said substrate, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour; and
(c) an activating agent applied to said coating in said first discrete area but not said second discrete area.

14. A method for forming a device for monitoring plural functions of goods comprising the steps of:
(a) providing a substrate;
(b) applying to said substrate a universal bar code comprising a number of discrete bars, some of said bars being printed with a polydiacetylene coating, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour;
(c) applying said polydiacetylene coating to said substrate in an area spaced from said discrete bars printed with said coating; and
(d) applying said activating agent to at least some but not all of said bars printed with said polydiacetylene coating.

15. A method for monitoring plural functions of goods comprising the steps of:
(a) providing a substrate having first and second discrete areas;
(b) applying diacetylene monomer to said first and second discrete areas;
(c) polymerizing said monomer to form a coating of polydiacetylene, said coating having properties of (1) changing from a first color irreversibly to a second color immediately upon being subjected to a specified temperature and (2), upon activation upon contact by an activating agent, changing from said first color to said second color at a temperature lower than said specified temperature after a time delay of at least one hour;
(d) applying said activating agent to said first discrete but not to said second discrete area;
(e) maintaining or bringing said substrate to a temperature below said specified temperature to cause that portion of the substrate contacted by said first discrete area to change to said second color; and
(f) thereafter heating said substrate to said specified temperature to cause that portion of the substrate within said second discrete area to change color.

16. The method according to claim 15 further including the step of affixing said coated substrate to goods or to a container holding said goods.

* * * * *